United States Patent
Olde et al.

(10) Patent No.: US 9,289,545 B2
(45) Date of Patent: Mar. 22, 2016

(54) CONTROLLING AN APPARATUS FOR FLUID TRANSFER TO AND/OR FROM A SUBJECT

(75) Inventors: Bo Olde, Lund (SE); Kristian Solem, Kavlinge (SE); Thomas Hertz, Lund (SE); Jan Sternby, Lund (SE); Anders Wieslander, Lund (SE)

(73) Assignee: Gambro Lundia AB, Lund (SE)

( * ) Notice: Subject to any disclaimer, the term of this patent is extended or adjusted under 35 U.S.C. 154(b) by 707 days.

(21) Appl. No.: 13/519,148

(22) PCT Filed: Dec. 22, 2010

(86) PCT No.: PCT/EP2010/070547
§ 371 (c)(1),
(2), (4) Date: Aug. 23, 2012

(87) PCT Pub. No.: WO2011/080186
PCT Pub. Date: Jul. 7, 2011

(65) Prior Publication Data
US 2013/0172803 A1 Jul. 4, 2013

Related U.S. Application Data

(60) Provisional application No. 61/290,304, filed on Dec. 28, 2009.

(30) Foreign Application Priority Data

Dec. 28, 2009 (SE) .................................... 0951023-1

(51) Int. Cl.
*A61M 1/30* (2006.01)
*A61B 5/0215* (2006.01)
(Continued)

(52) U.S. Cl.
CPC ................ *A61M 1/30* (2013.01); *A61B 5/0215* (2013.01); *A61B 5/02405* (2013.01);
(Continued)

(58) Field of Classification Search
USPC ................................................ 604/6.01, 6.11
See application file for complete search history.

(56) References Cited

U.S. PATENT DOCUMENTS 5,670,050 A * 9/1997 Brose ........................ A61L 2/04
210/646
6,663,585 B1 12/2003 Ender
(Continued)

FOREIGN PATENT DOCUMENTS

JP 2005027801 2/2005
WO WO 97/10013 3/1997
(Continued)

*Primary Examiner* — Tatyana Zalukaeva
*Assistant Examiner* — Guy K Townsend
(74) *Attorney, Agent, or Firm* — Mueting, Raasch & Gebhardt, P.A.

(57) ABSTRACT

A control system (23) is arranged to control the operation of an apparatus (200) for extracorporeal blood treatment. The apparatus (200) comprises an extracorporeal blood circuit (20) and a connection system (C) for connecting the blood circuit (20) to the vascular system of a patient. The blood circuit (20) comprises a blood processing device (6), and at least one pumping device (3). The control system is operable to switch between a pre-treatment mode and a blood treatment mode. The blood treatment mode involves operating the blood circuit (20) to pump blood from the vascular system via the connection system (C) through the blood processing device (6) and back to the vascular system via the connection system (C). The control system (23) is operable to obtain measurement data from at least one energy transfer sensor (40) arranged to sense a transfer of energy between the patient and the connection system (C) or between the patient and the blood circuit (20). The control system (23) is configured to, in the pre-treatment mode, process the measurement data for identification of a characteristic change indicating a connection of the blood circuit (20) to the vascular system of the patient, and, upon such identification, take dedicated action. The action may involve activating at least part of a patient protection system and/or enabling entry into the blood treatment mode. The control system may be included in an apparatus (200) for blood treatment, such as a dialysis machine.

15 Claims, 13 Drawing Sheets

(51) Int. Cl.
    *A61B 5/024*     (2006.01)
    *A61B 5/00*     (2006.01)
    *A61M 1/36*     (2006.01)

(52) U.S. Cl.
    CPC ........... *A61B 5/4836* (2013.01); *A61M 1/3653* (2013.01); *A61M 1/3656* (2013.01); *A61M 1/3643* (2013.01); *A61M 2205/3331* (2013.01); *A61M 2205/6018* (2013.01)

(56) References Cited

U.S. PATENT DOCUMENTS

| | | |
|---|---|---|
| 6,932,786 B2 | 8/2005 | Giacomelli |
| 8,715,216 B2 | 5/2014 | Olde |
| 2003/0152482 A1 | 8/2003 | O'Mahony et al. |
| 2003/0194894 A1 | 10/2003 | Wariar et al. |
| 2003/0195453 A1 | 10/2003 | Han |
| 2004/0186409 A1* | 9/2004 | Cavalcanti ......... A61M 1/3621 604/4.01 |
| 2005/0004582 A1* | 1/2005 | Edoga ................. A61B 17/10 606/139 |
| 2005/0010118 A1 | 1/2005 | Toyoda et al. |
| 2007/0000847 A1 | 1/2007 | Ross |
| 2007/0112289 A1* | 5/2007 | Cavalcanti ......... A61M 1/3621 604/4.01 |
| 2009/0082676 A1* | 3/2009 | Bennison ........... A61M 1/3653 600/462 |
| 2009/0088683 A1 | 4/2009 | Roger et al. |
| 2011/0106466 A1 | 5/2011 | Furmanski |
| 2012/0165848 A1* | 6/2012 | Slayton .................. A61N 7/02 606/169 |
| 2013/0172803 A1* | 7/2013 | Olde ................... A61B 5/0215 604/6.11 |
| 2013/0199998 A1* | 8/2013 | Kelly .................. A61M 1/1696 210/646 |
| 2015/0019170 A1 | 1/2015 | Solem |

FOREIGN PATENT DOCUMENTS

| | | |
|---|---|---|
| WO | WO 01/47581 | 7/2001 |
| WO | WO 2004/067064 A1 | 8/2004 |
| WO | WO 2007/141246 A1 | 12/2007 |
| WO | WO 2009/038834 A1 | 3/2009 |
| WO | WO 2009/156175 | 12/2009 |

* cited by examiner

US 9,289,545 B2

CONTROLLING AN APPARATUS FOR FLUID TRANSFER TO AND/OR FROM A SUBJECT

This application is a U.S. National Stage Application of International Application No. PCT/EP2010/070547, filed Dec. 22, 2010, which was published in English on Jul. 7, 2011 as International Patent Publication WO 2011/080186 A1, and which claims the benefit under 35 U.S.C. 119(e) of U.S. Provisional Application No. 61/290,304, filed Dec. 28, 2009. International Application No. PCT/EP2010/070547 also claims priority to Swedish Application No. 0951023-1, filed Dec. 28, 2009.

TECHNICAL FIELD

The present invention generally relates to an apparatus for fluid transfer to and/or from a human or animal subject, and in particular to techniques for controlling the operation of such an apparatus. The present invention is e.g. applicable in relation to an apparatus for extracorporeal blood treatment such as a dialysis machine.

BACKGROUND ART

The preparation before starting a fluid transfer to and/or from a subject with the use of dedicated apparatus, e.g. a dialysis machine, involves many manual handling steps. The large number of steps takes both time and effort from the medical staff, and offers a potential for human mistakes and errors and thus poses a risk to the subject.

SUMMARY

It is an object of the invention to at least partly overcome one or more of the above-identified limitations of the prior art. Specifically, it is an object to provide a technique that simplifies or facilitates the start-up procedure in connection with a fluid transfer to/from a subject by means of a dedicated fluid transfer apparatus. It is also an object to at least not reduce, and preferably improve, the safety of the patient.

This and other objects, which will appear from the description below, are at least partly achieved by means of control systems, methods, and computer-readable media according to the independent claims, embodiments thereof being defined by the dependent claims.

A first aspect of the invention is a control system in an apparatus for extracorporeal blood treatment, wherein said apparatus comprises an extracorporeal blood circuit and a connection system for connecting the extracorporeal blood circuit to the vascular system of a patient, wherein the extracorporeal blood circuit comprises a blood processing device, and at least one pumping device, said control system being operable to switch between a pre-treatment mode and a blood treatment mode, wherein the blood treatment mode involves operating said at least one pumping device to pump blood from the vascular system via the connection system through the blood processing device and back to the vascular system via the connection system, said control system comprising: an input for obtaining measurement data from at least one energy transfer sensor arranged to sense a transfer of energy between the patient and the connection system or between the patient and the extracorporeal blood circuit, and a signal processor connected to the input and being configured to, in the pre-treatment mode, process the measurement data for identification of a characteristic change indicating a connection of the extracorporeal blood circuit to the vascular system of the patient, and, upon such identification, take a dedicated action.

A second aspect of the invention is a control system in an apparatus for extracorporeal blood treatment, wherein said apparatus comprises an extracorporeal blood circuit and a connection system for connecting the extracorporeal blood circuit to the vascular system of a patient, wherein the extracorporeal blood circuit comprises a blood processing device, and at least one pumping device, said control system being operable to switch between a pre-treatment mode and a blood treatment mode, wherein the blood treatment mode involves operating said at least one pumping device to pump blood from the vascular system via the connection system through the blood processing device and back to the vascular system via the connection system, said control system comprising: means for obtaining measurement data from at least one energy transfer sensor arranged to sense a transfer of energy between the patient and the connection system or between the patient and the extracorporeal blood circuit, means for processing, when the control system is in the pre-treatment mode, the measurement data for identification of a characteristic change indicating a connection of the extracorporeal blood circuit to the vascular system of the patient, and means for causing a dedicated action upon such identification.

A third aspect of the invention is a method for controlling an apparatus for extracorporeal blood treatment, wherein said apparatus comprises an extracorporeal blood circuit and a connection system for connecting the extracorporeal blood circuit to the vascular system of a patient, wherein the extracorporeal blood circuit comprises a blood processing device, and at least one pumping device, wherein said apparatus is operable in a pre-treatment mode and a blood treatment mode, wherein the blood treatment mode involves operating said at least one pumping device to pump blood from the vascular system via the connection system through the blood processing device and back to the vascular system via the connection system, said method comprising: obtaining measurement data from at least one energy transfer sensor which is arranged to sense a transfer of energy between the patient and the connection system or between the patient and the extracorporeal blood circuit, while operating the apparatus in the pre-treatment mode, processing the measurement data for identification of a characteristic change indicating a connection of extracorporeal blood circuit to the vascular system of the patient, and upon such identification, causing a dedicated action to be taken.

A fourth aspect of the invention is a computer-readable medium comprising computer instructions which, when executed by a processor, cause the processor to perform the method of the third aspect.

A fifth aspect of the invention is a control system in an apparatus for fluid transfer to or from a subject, wherein said apparatus comprises a fluid circuit and a connection system for connecting the fluid circuit to the vascular system of the subject, wherein the fluid circuit comprises a fluid pathway and at least one pumping device, said control system being operable to switch between a preparatory mode and a fluid transfer mode, wherein the fluid transfer mode involves operating the fluid circuit to transfer a fluid to or from the vascular system via the connection system and the fluid pathway, said control system comprising: an input for obtaining measurement data from at least one energy transfer sensor arranged to sense a transfer of energy between the subject and the connection system or between the subject and the fluid circuit, and a signal processor connected to the input and being configured to, in the preparatory mode, process the measurement data for identification of a characteristic change indicating a connection of the fluid circuit to the vascular system of the subject, and, upon such identification, take dedicated action.

A sixth aspect of the invention is a control system in an apparatus for fluid transfer to or from a subject, wherein said apparatus comprises a fluid circuit and a connection system for connecting the fluid circuit to the vascular system of the subject, wherein the fluid circuit comprises a fluid pathway and at least one pumping device, said control system being operable to switch between a preparatory mode and a fluid transfer mode, wherein the fluid transfer mode involves operating the fluid circuit to transfer a fluid to or from the vascular system via the connection system and the fluid pathway, said control system comprising: means for obtaining measurement data from at least one energy transfer sensor arranged to sense a transfer of energy between the subject and the connection system or between the subject and the fluid circuit, means for processing, when the control system is in preparatory mode, the measurement data for identification of a characteristic change indicating a connection of the fluid circuit to the vascular system of the subject, and means for causing a dedicated action upon such identification.

A seventh aspect of the invention is a method for controlling an apparatus for fluid transfer to or from a subject, wherein said apparatus comprises a fluid circuit and a connection system for connecting the fluid circuit to the vascular system of a subject, wherein the fluid circuit comprises a fluid pathway and at least one pumping device, wherein said apparatus is operable in a preparatory mode and a fluid transfer mode, wherein the fluid transfer mode involves operating the fluid circuit to transfer a fluid to or from the vascular system via the connection system and the fluid pathway, said method comprising: obtaining measurement data from at least one energy transfer sensor which is arranged to sense a transfer of energy between the subject and the connection system or between the subject and the fluid circuit, while operating the apparatus in the preparatory mode, processing the measurement data for identification of a characteristic change indicating a connection of fluid circuit to the vascular system of the subject, and upon such identification, causing a dedicated action to be taken.

An eighth aspect of the invention is a computer-readable medium comprising computer instructions which, when executed by a processor, cause the processor to perform the method of the seventh aspect.

Still other objectives, features, aspects and advantages of the present invention will appear from the following detailed description, from the attached claims as well as from the drawings.

BRIEF DESCRIPTION OF THE DRAWINGS

Exemplary embodiments of the invention will now be described in more detail with reference to the accompanying schematic drawings.

DETAILED DESCRIPTION OF EXEMPLARY EMBODIMENTS

In the following, embodiments will be described with reference to an apparatus for extracorporeal blood treatment. In particular, exemplary embodiments for controlling the apparatus before and during blood treatment are described. A description is also given of various detection techniques that may be used to provide system data for such control, as well as specific embodiments for processing pressure signals obtained from the apparatus. Throughout the following description, like elements are designated by the same reference signs.

I. Example of an Extracorporeal Circuit

Figure 1:
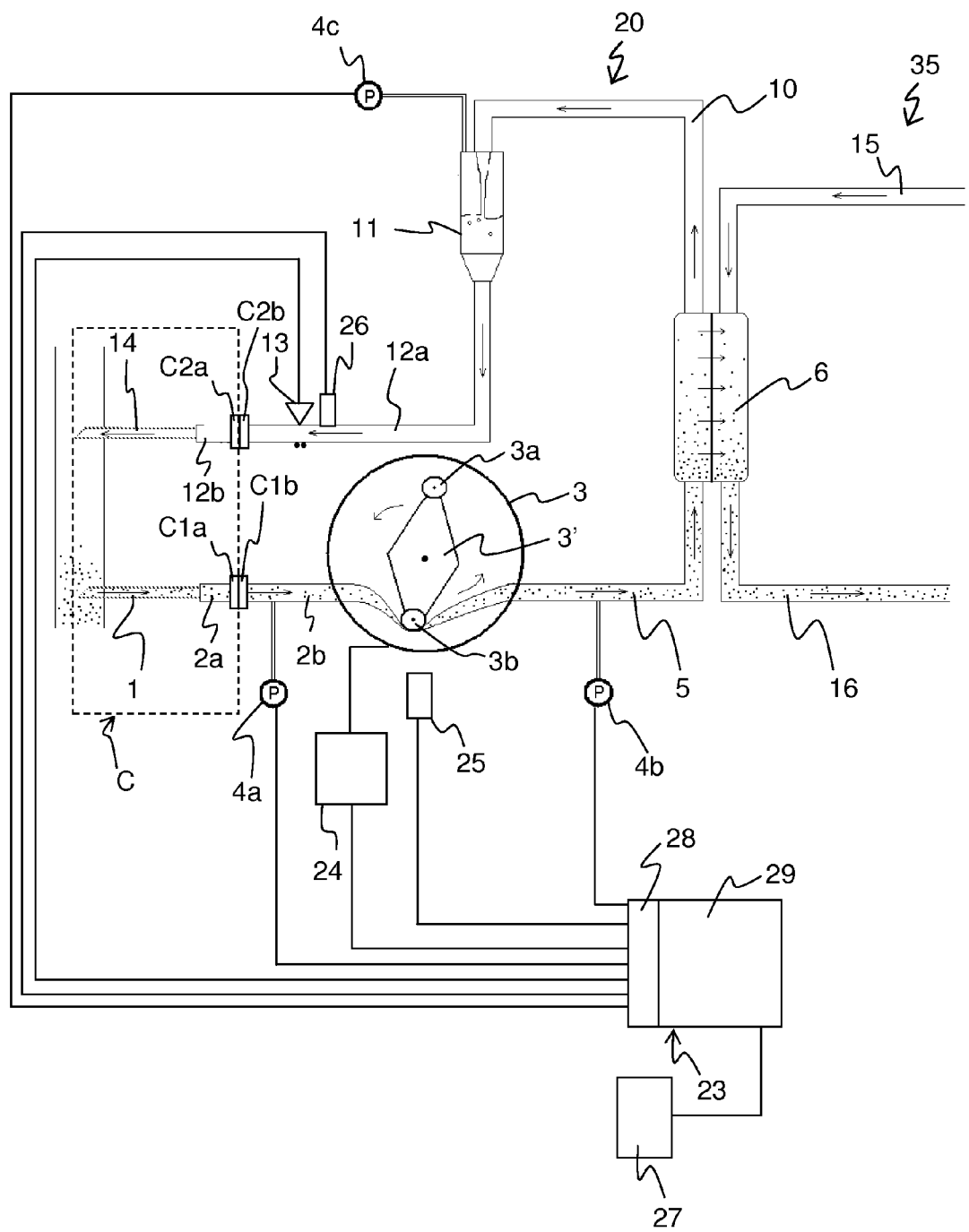
FIG. 1 is a schematic view of a system for hemodialysis treatment including an extracorporeal blood flow circuit.

FIG. 1 shows an example of an extracorporeal blood flow circuit 20, which is part of an apparatus for blood treatment, in this case a dialysis machine. The extracorporeal circuit 20 is connected to the vascular system of a patient by means of a connection system C. The connection system C comprises an arterial access device 1 for blood extraction (here in the form of an arterial needle), a connection tube segment 2$a$ and a connector C1$a$. The connection system C also comprises a venous access device 14 for blood reintroduction (here in the form of a venous needle), a connection tube segment 12$b$, and a connector C2$a$. The connectors C1$a$, C2$a$ are arranged to provide a releasable or permanent engagement with a corresponding connector C1$b$, C2$b$ in the circuit 20 so as to form a blood path between the circuit 20 and the arterial needle 1 and the venous needle 14, respectively. The connectors C1$a$, C1$b$, C2$a$, C2$b$ may be of any known type.

In the illustrated example, the extracorporeal circuit 20 comprises the connector C1$b$, an arterial tube segment 2$b$, and a blood pump 3 which may be of peristaltic type, as indicated in FIG. 1. At the inlet of the pump there is a pressure sensor 4a (hereafter referred to as arterial sensor) which measures the pressure before the pump in the arterial tube segment 2b. The blood pump 3 forces the blood, via a tube segment 5, to the blood-side of a dialyser 6. In many dialysis machines, the circuit 20 is additionally provided with a pressure sensor 4b that measures the pressure between the blood pump 3 and the dialyser 6. The blood is led via a tube segment 10 from the blood-side of the dialyser 6 to a venous drip chamber or deaeration chamber 11 and from there back to the connection system C via a venous tube segment 12a and the connector C2b. A pressure sensor 4c (hereafter referred to as venous sensor) is provided to measure the pressure on the venous side of the dialyser 6. In the illustrated example, the pressure sensor 4c measures the pressure in the venous drip chamber 11. Both the arterial needle 1 and the venous needle 14 are connected to the vascular system of a human or animal patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters.

Herein, the "venous side" of the extracorporeal circuit 20 refers to the part of the blood path located downstream of the blood pump 3, whereas the "arterial side" of the extracorporeal circuit 20 refers to the part of the blood path located upstream of the blood pump 3. In the example of FIG. 1, the venous side is made up of tube segment 5, the blood-side of the dialyser 6, tube segment 10, drip chamber 11 and tube segment 12a, and the arterial side is made up of tube segment 2b.

The dialysis machine also includes a dialysis fluid circuit 35, which is only partly shown in FIG. 1 and which is operated to prepare, condition and circulate dialysis fluid through the dialysis fluid-side of the dialyser 6, via tube segments 15, 16.

Further, in FIG. 1, a main controller 23 is arranged to control the operation of the dialysis machine. For example, the main controller 23 controls the operation of the extracorporeal circuit 20, e.g. by controlling the blood flow through the circuit 20 via the revolution speed of the blood pump 3 (e.g. by means of a dedicated pump controller 24), and the opening and closing of various flow controllers such as valves, clamping devices, etc (collectively represented by clamping device 13 in FIG. 1). Similarly, the main controller 23 controls the operation of the dialysis fluid circuit 35. Although not shown or discussed further, it is to be understood that the main controller 23 may be configured to control many other functions of the dialysis machine, e.g. controlling the temperature and composition of the dialysis fluid, generating feedback or instructions to the operator of the machine, etc.

The main controller 23 is also connected to acquire output signals from various sensors, for use in controlling the operation of the dialysis machine. Such sensors include the pressure sensors 4a-4c in the circuit 20, pressure sensors (not shown) in the dialysis fluid circuit 35, as well as a pump sensor 25, such as a rotary encoder (e.g. conductive, optical or magnetic) or the like, for indicating the frequency and/or phase of the blood pump 3. Alternatively or additionally, the pump sensor 25 may be connected directly to the pump controller 24 for use in controlling the revolution speed of the blood pump 3. Another such sensor is a priming sensor 26, which is configured to indicate presence or absence of blood at a particular location on the venous-side of the circuit, typically on the tube segment 12a close to the venous-side clamp 13.

The main controller 23 may also execute safety functions, in which it acquires and analyses the output signals of a number of dedicated or general sensors in the dialysis machine for identification or prevention of one or more fault conditions. The safety functions may collectively form a "patient protection system". For example, dialysis machines often include a dedicated blood leakage sensor which is arranged in the dialysis fluid circuit 35 to sense leakage of blood from the extracorporeal circuit 20 into the dialysis fluid circuit 35 via the dialyser 6. Another dedicated sensor is an air detector which is arranged in the extracorporeal circuit 20 to detect air bubbles in the blood flow. It is also e.g. known to attach a PPG sensor (Photoplethysmograph) to the patient, for predicting hypotension in the patient, e.g. as described in WO2007/141246. Furthermore, the output signals of one or more of the pressure sensors 4a-4c (as well as pressure sensors in the dialysis fluid circuit 35) may be processed for identification of fault conditions, e.g. in the connection system C, the extracorporeal circuit 20, the dialysis fluid circuit 35, or the patient. One such fault condition is dislodgement of the venous or arterial access device 1, 14 from the blood vessel access, i.e. that the access device comes loose from the vascular system of the patient. Another fault condition is disconnection of the venous or arterial access device 1, 14 from the circuit 20, typically by disruption/defective coupling/uncoupling of the connectors C1a, C1b and C2a, C2b, respectively. Yet another safety function based on output signals of the pressure sensors 4a-4c involve detecting if the static pressure in the blood (DC pressure level) falls outside upper and lower pressure limits, which are predetermined or set by the operator of the dialysis machine or automatically adjusted in response to manual changes of the blood flow rate.

The detection of a fault condition may bring the main controller 23 to activate an alarm and/or stop the blood flow, e.g. by stopping the blood pump 3 and activating one or more clamping devices (cf. 13) on the tube segments 2a, 2b, 5, 10, 12a, 12b. The main controller 23 may also be tethered or wirelessly connected to a local or remote device 27 for generating an audible/visual/tactile alarm or warning signal. The alarm device 27 may alternatively be incorporated in the dialysis machine.

In the example of FIG. 1, the main controller 23 comprises an input/output (I/O) part 28 for sampling measurement data from various sensors included in, or otherwise associated with, the dialysis machine, and for transmitting control signals to the various components included in, or otherwise associated with, the dialysis machine. The I/O part 28 may also be configured to pre-process the measurement data. For example, the I/O part 28 may include an A/D converter with a required minimum sampling rate and resolution, and one or more signal amplifiers. Generally, the measurement data is a time sequence of data samples, each representing an instantaneous sensor value. The I/O part 28 generates a number of measurement signals (e.g. one or more pressure signals), which are provided as input to a data analysis part 29 that executes the actual system control. Depending on implementation, the main controller 23 may use digital components or analog components, or a combination thereof, for acquiring, processing and analysing the measurement data.

The main controller 23 may operate the dialysis machine in several different modes. For the purpose of the present description, these modes are conceptually divided into two main groups: "pre-treatment" and "blood treatment".

The pre-treatment mode is any mode that may precede the blood treatment mode. The dialysis machine remains in the pre-treatment mode as long as no blood is circulated back to the patient from the circuit 20. As will be explained in more detail below, the pre-treatment mode may involve blood being drawn from the patient into the circuit 20, as part of the process of connecting the venous needle 14 to the blood access. In the pre-treatment mode, there may not be a need for all of the safety functions, e.g. since certain fault conditions might not pose an immediate threat to the patient or cannot be detected by the sensor(s). Therefore, all or a large part of the safety functions of the main controller 23 are typically disabled (but need not be) in the pre-treatment mode.

In the blood treatment mode, blood is drawn from the patient into the extracorporeal circuit 20 and pumped back to the patient after treatment. All safety functions of the main controller 23 are active. It is to be understood that the blood pump 3 may be intermittently stopped during the blood treatment mode, such that temporarily no blood is drawn from or pumped back to the vascular system of the patient. Generally, the dialysis machine remains in the blood treatment mode during these pump stops, and the safety functions of the main controller 23 remain active.

Embodiments of the invention relate to the system control carried out by the main controller 23, based on measurement data from one or more energy transfer sensors, i.e. a sensor that is capable of sensing a transfer of energy between the patient and the connection system C, and/or between the patient and the extracorporeal circuit 20.

II. System Control Based on Energy Transfer Measurement

Figure 2:
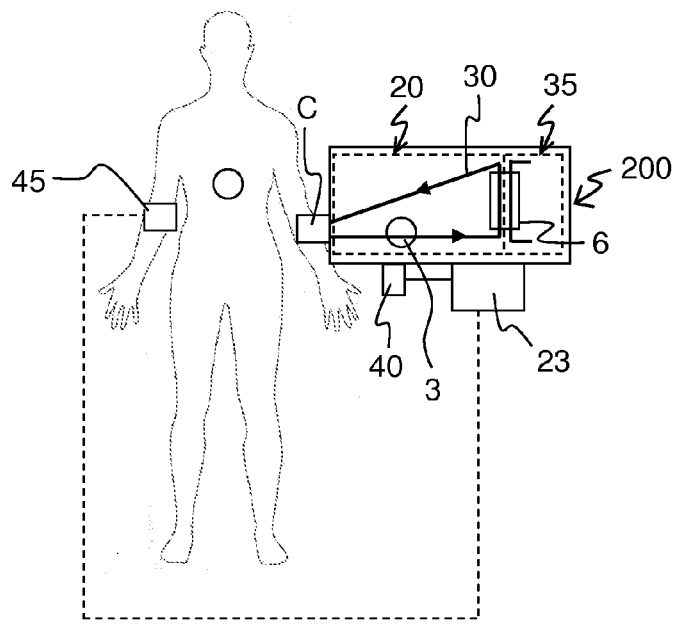
FIG. 2 is a generalized block diagram of an apparatus for blood treatment connected to a subject.

FIG. 2 is a generalized illustration of an apparatus 200 for extracorporeal blood treatment (e.g. a dialysis machine), in which an extracorporeal blood flow circuit 20 is connected to the vascular system of a patient by means of a connection system C. The extracorporeal circuit 20 includes one or more blood pumps 3, the blood-side of a blood processing device 6, and a blood path 30 extending from the connection system C through the blood pump(s) 3 and the blood processing device 6 and back to the connection system C. In FIG. 2, the apparatus 200 also comprises a dialysis fluid circuit 35, which includes the dialysis fluid-side of the blood processing device 6. A main controller 23 is connected to, or part of, the apparatus 200 to control its operation. An energy transfer sensor 40 is connected to the apparatus 200, typically to either of the extracorporeal circuit 20 and the connection system C, to sense a transfer of energy from the patient to the connection system C, and possibly also to the extracorporeal circuit 20. Alternatively (not shown), the energy transfer sensor 40 may be arranged on the patient to sense a transfer of energy from the extracorporeal circuit 20 and/or the connection system C to the patient.

Embodiments of the invention uses the measurement data provided by the energy transfer sensor 40 to control the operation of the apparatus 200. In particular, the operation of the apparatus 200 is controlled based on a detected transfer of energy in the measurement data, if the transfer of energy indicates that a fluid connection has been established between the vascular system of the patient and the extracorporeal blood circuit 20.

Figure 3:
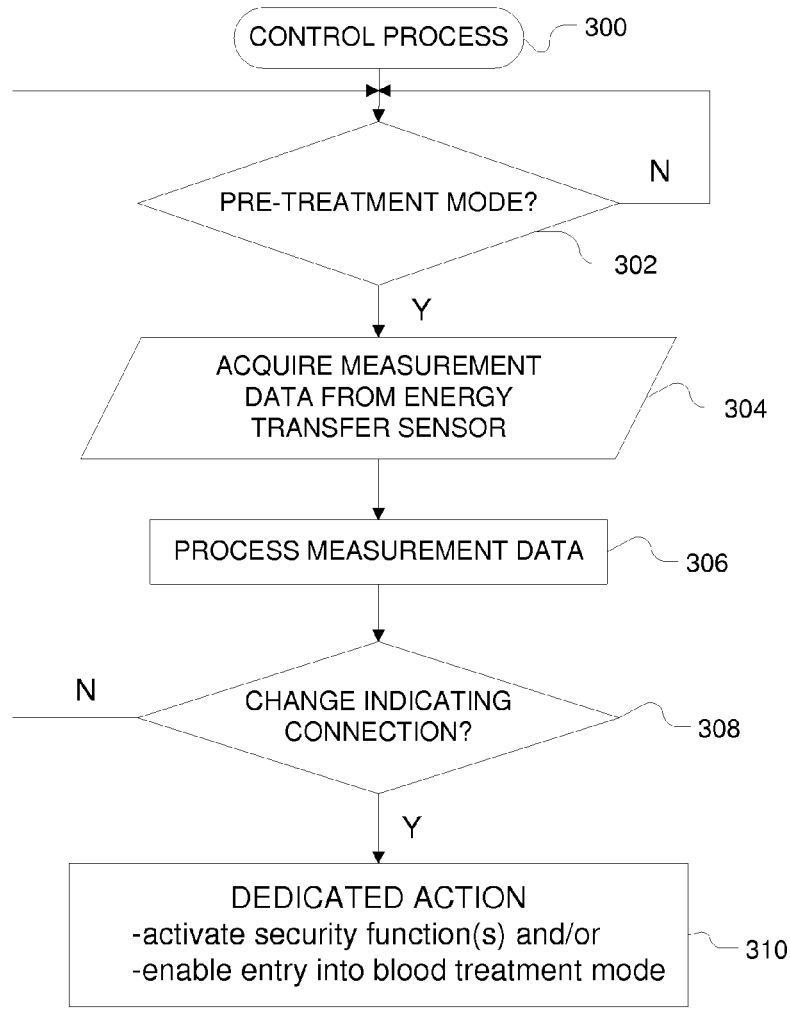
FIG. 3 is a flow chart of a process for controlling the operation of the apparatus in FIG. 2

FIG. 3 is a flow chart of an embodiment of a process 300 for controlling the apparatus 200 in FIG. 2. In the illustrated example, the method repeatedly iterates through a sequence of steps 302-308. Also, the process 300 presumes that the apparatus 200 initially is operable to enter the pre-treatment mode (and not the blood treatment mode).

In step 302, it is determined whether the apparatus 200 is in the above-mentioned pre-treatment mode. If not, the process returns to start a new iteration. If in pre-treatment mode, the process continues to step 304, in which a set of measurement data is acquired from the energy transfer sensor 40 (e.g. via the I/O part 28 in FIG. 1). The measurement data is then processed in step 306 for identification of a characteristic change in the measurement data. Step 306 may involve calculating a specific parameter value. The parameter value is selected to represent a change caused by a desired connection of extracorporeal circuit 20 and/or the connection system C to the patient.

Specifically, if the energy transfer sensor 40 is arranged on the apparatus 200, the characteristic change may originate from the patient itself or from an energy source attached to the patient. If the energy transfer sensor 40 is arranged on the patient, the characteristic change may originate from an energy source in, or attached to, the extracorporeal system 20 or the connection system C. In one embodiment, the energy transfer sensor 40 is a pressure sensor, and the energy source is a pressure wave generator. In another embodiment, the energy transfer sensor 40 is a sensor for measuring electrical current, voltage, capacitance, or an equivalent quantity, and the energy source is an electrical energy source, such as a current or voltage generator.

In step 308, the parameter value is evaluated to determine if the characteristic change is present. This may involve comparing the parameter value to a threshold value or a range. The threshold value/range may be pre-set or predetermined or may be given by one or more parameter values calculated in preceding iterations.

If no characteristic change is identified in step 308, the process returns to start a new iteration. If the characteristic change is detected, the process continues to step 310 to take a dedicated action. This action may, e.g., involve activating one or more of the above-mentioned safety functions and maintaining the apparatus 200 in the pre-treatment mode, or activating the safety function(s) and allowing the apparatus 200 to enter the blood treatment mode.

In a variant, step 308 is configured to discriminate between "certain connection" which corresponds to positive detection of the characteristic change, and "possible connection" which corresponds to less certain detection of the characteristic change. For example, "certain connection" and "possible connection" may be concluded when the parameter value falls within a first range and a second range, respectively, wherein the first range is a sub-set of the second range. If a "possible connection" is concluded, step 310 may cause a dedicated action, such as requiring confirmation from the operator, e.g. via a control panel/display, or to replace or supplement the energy transfer sensor and energy source already in use by causing measurement data to be acquired from another energy transfer sensor and/or by activating another energy source.

Generally, it may be advantageous to arrange the energy transfer sensor 40 and the energy source (or to use more than one energy transfer sensor or energy source) so as to be able to separately determine connection of the arterial side and the venous side of the extracorporeal circuit 20, respectively, to the patient. This will enable different actions (including no action) to be taken for different connection states: venous side connected, arterial side connected and both venous and arterial sides connected.

In the following, different actions will be further explained and exemplified in relation to a number of examples. The examples are all based on the use of one or more pressure sensors (cf. 4a-4c in FIG. 1) in the extracorporeal circuit 20 as energy transfer sensor(s), and the heart of the patient as a pressure wave generator.

Figure 4:
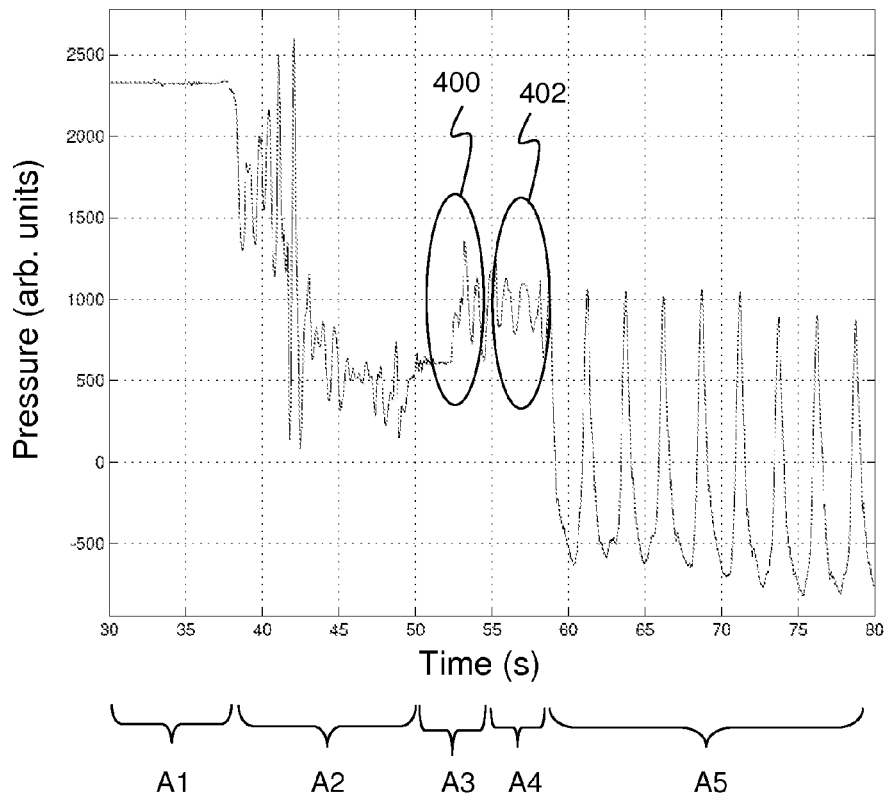
FIG. 4 a plot of a pressure signal acquired from a sensor in the system of FIG. 1 during connection of the extracorporeal blood flow circuit to the subject.

To illustrate the feasibility of such an embodiment, FIG. 4 illustrates a pressure signal acquired from the arterial sensor 4a in the circuit 20 of FIG. 1 during a connection of the arterial side to the patient. The connection procedure has been divided into time sections A1-A5. In section A1, which represents the end stage of a priming procedure, the connector C1b is connected to a source of priming liquid and the venous tube segment 12a is closed off by a manual clamp (typically not clamp 13 in FIG. 1) and connected to a waste container, and the blood pump 3 has been stopped. In section A2, the arterial tube segment 2b is manually clamped and disconnected from the source of priming liquid and moved to the connection system C, where connector C1b is attached to connector C1a. The arterial needle 1 has previously been inserted into the fistula of the patient, and to prevent blood from leaving the patient, a manual clamp has been attached to close off the arterial tube segment 2a. In section A3, all three manual clamps are opened (on tube segments 12a, 2b and 2a), which results in a step change of the pressure on the arterial side of the extracorporeal circuit 20, as measured by the arterial sensor 4a. This step change (encircled at 400) may be thus detected to indicate the connection of the extracorporeal circuit 20 to the patient. In section A4, the pressure wave caused by the opening of the manual clamps settles, and pulsations originating from the patent's heartbeats are visible in the pressure signal. These pulsations (encircled at 402) form a characteristic change in the pressure signal that may be detected, instead of or in addition to the step change, to indicate the connection between the extracorporeal circuit 20 and the patient. In section A5, the blood pump 3 is started to draw blood from the patient into the extracorporeal circuit 20. Now, pulsations originating from the blood pump 3 dominate the pressure signal.

In one example, the process in FIG. 3 is performed when the apparatus 200 is operated according to a priming program. During priming, the arterial-side connector C1b is attached to a source of priming liquid, and the venous-side connector C2b is arranged in fluid communication with a drain or a waste container for collecting spent priming liquid. The priming program operates the blood pump 3 to pump priming liquid from the source to the drain/waste container. During the priming program, it is important to ascertain that neither connector C1b, C2b is inadvertently attached to the connectors C1a, C2a of the connection system C, since this may lead to either excessive drawing of blood out of the patient or excessive pumping of priming liquid into the patient. Reverting to the method of FIG. 3, step 310 may involve stopping the blood pump, or otherwise stopping the flow of priming liquid, e.g. by activating a machine-controlled clamp to close off the blood path through the circuit 20, when step 308 indicates that a characteristic change has been identified in either the pressure signal from the arterial sensor 4a, or the pressure signal from the venous sensor 4c, or both. In this example, the blood pump is active during steps 304-308 in FIG. 3.

In another example, the process in FIG. 3 is performed when the apparatus 200 is operated according to a post-priming program, i.e. when the arterial-side and venous-side connectors C1b, C2b are disconnected from the connection system C (possibly attached to the aforesaid source and waste container, respectively), and the blood pump 3 is shut off. Following standard procedure, the operator first attaches the arterial-side connector C1b to the connector C1a, while the venous-side connector C2b remains connected to the waste container. When step 308 indicates that a characteristic change has been identified in the pressure signal from the arterial sensor 4a, step 310 may cause the blood pump 3 to be started to draw blood through the arterial needle 1 into the extracorporeal circuit 20. Step 310 may also cause all or part of the safety functions of the apparatus 200 to be activated. It is, however, conceivable that one or more safety functions are activated before step 310, e.g. safety functions that are activated automatically at start-up of the apparatus 200. Step 310 may involve activating a special safety function designed to eliminate patient risks caused by a failure in the priming detector 26. The blood pump 3 is kept running until the priming detector 26 indicates blood, i.e. until the extracorporeal circuit 20 has been at least partly filled with blood and purged from priming liquid. The special safety function may be designed to estimate the amount of blood drawn out of the patient, e.g. by dead reckoning the pump revolutions (e.g. based on the output signal of the pump sensor 25), and to shut off the blood pump 3 if the estimated amount exceeds a predetermined limit value. When the priming detector 26 indicates blood, the blood pump 3 is shut off, and the operator connects the venous-side connector C2b to the connector C2a. When step 308 indicates that a characteristic change has been identified in both the pressure signal from the arterial sensor 4a and the pressure signal from the venous sensor 4c, step 310 may enable start of a blood treatment program, which either automatically starts the blood pump 3 and opens the machine-controlled clamps, or allows the operator to start the blood pump 3 by pressing a start button. Step 310 may also, if not already done, activate all safety functions.

The foregoing example is also applicable to an alternative procedure, in which the operator starts by attaching the venous-side connector C2b to the connector C1a, with the intention of filling at least part of the extracorporeal circuit 20 with blood. When step 308 indicates that a characteristic change has been identified in the pressure signal from the venous sensor 4c, step 310 may cause the blood pump 3 to be started to draw blood through the arterial needle 1 into the extracorporeal circuit 20 and/or cause one or more safety functions to be activated. In another alternative procedure, the operator starts by attaching both connectors C1a, C2b to connection system C. Like in the foregoing example, when step 308 indicates that a characteristic change has been identified in the pressure signal from one or both of the sensors 4a, 4c, step 310 may cause the dialysis machine to draw blood through the needles 1, 14 into the extracorporeal circuit 20 and/or cause the safety function(s) to be activated. It is realized that such a procedure may require a different configuration of the dialysis machine compared to FIG. 1.

In another example, the process in FIG. 3 is performed when the apparatus 200 is operated according to another post-priming program, which does not operate the blood pump 3 to purge a major part of the priming liquid as in the foregoing example, but instead allows the operator to attach an extracorporeal circuit 20 filled with priming liquid to the connection system C (e.g. by connecting connectors C1a, C1b and C2a, C2b, respectively, and by opening clamps at tubing segments 2a, 2b, 12a, 12b), while the blood pump 3 is shut off. When step 308 indicates that a characteristic change has been identified in both the pressure signal from the arterial sensor 4a and the pressure signal from the venous sensor 4c, step 310 may enable start of a blood treatment program, in which the blood pump 3 is started, as in the foregoing example, and activation of all safety functions.

In another example, the process in FIG. 3 is performed whenever the operator tries to start the blood pump 3, e.g. by pushing a start button on the apparatus 200. The pushing of the start button may cause the apparatus 200 to open one or more machine-controlled clamps, such that the pressure waves from the patient's heart are allowed to reach the pressure sensors 4a, 4c. If step 308 does not indicate a characteristic change in the pressure signal from either the arterial sensor 4a or the venous sensor 4c, step 310 may cause the apparatus to be operated according to a priming program. If step 308 indicates a characteristic change in the pressure signal from the arterial sensor 4a only, step 310 may cause the apparatus to be operated according a post-priming program, e.g. according to the example above. If step 308 indicates a characteristic change in the pressure signal from the venous sensor 4c only, step 310 may prevent start of the blood pump and possibly instruct the operator to check the connection system C. If step 308 indicates a characteristic change in the pressure signals from both the venous sensor 4a and the arterial sensor 4a, step 310 may cause the apparatus to be operated according a blood treatment program. Step 310 need not decide on a particular action only based on the outcome of step 308, but also on other factors, such as the preceding programs run by the apparatus or a specific program selection made by the operator on a control panel of the apparatus 200. For example, if the apparatus has run a priming program and a post-priming program, step 310 may prevent start of the blood pump 3 unless step 308 indicates a connection of both connectors C1b, C2b. The same applies if the operator has explicitly selected a blood treatment program on the control panel.

In a variant, the blood pump is started whenever the operator pushes the start button, and the process in FIG. 3 is performed in parallel, i.e. while the blood pump 3 is running. To reduce patient risk, the blood pump 3 may be operated with a reduced pumping frequency (flow rate). If step 308 indicates erroneous connection compared to the selected or expected treatment program, step 310 may cause the blood pump 3 to be shut down and the machine-controlled clamps to be closed. Otherwise, step 310 may increase the pumping frequency to generate a nominal or prescribed flow rate of blood through the circuit 20.

Whenever one or more machine-controlled clamps (or other mechanical flow blocking devices) are opened, pressure waves are generated which may interfere with the detection of the characteristic change according to steps 304-308. Thus, it may be beneficial to delay steps 304-308 until such pressure waves have subsided, which usually takes place within one or a few seconds.

In certain of the examples given above, the blood pump 3 is shut off during steps 304-308 which facilitates the detection of the characteristic change. If the blood pump 3 is running during steps 304-308, the pressure waves generated by the blood pump may make it more difficult to detect the characteristic change. Section V, below, discloses different techniques for enabling detection of the characteristic change when the blood pump is running.

III. Examples of Energy Transfer Sensors and Energy Sources

The transfer of energy may be sensed by any type of sensor 40 (FIG. 2) capable of sensing energy in any form. Similarly, any type of energy source may generate the energy.

In one simple embodiment, a mechanical switch is arranged on the connection system C, e.g. on one or both of the needles 1, 14, to sense when the connection system C is connected to the patient. Thus, the energy source is the mechanical action of inserting the needle 1, 14 into the fistula of the patient.

However, to improve the certainty of detection, it may be desirable to sense the transfer of energy originating from an energy source with a more predictable output of energy. Thus, a separate energy source may be attached to either the patient or the apparatus 200, while the energy transfer sensor 40 may be provided in the apparatus 200 and the patient, respectively. Instead of requiring a separate energy source, the energy transfer sensor 40 may be arranged to detect energy from an inherent energy source in either the patient or the apparatus 200.

The energy transfer sensor 40 may be a separate, dedicated sensor which is attached to the patient, the connection system C, or the extracorporeal system 20. Alternatively, an inherent sensor in the connection system C or the extracorporeal circuit 20 is used as the energy transfer sensor 40.

When the energy source is provided in (or attached to) the patient, it may be beneficial for the energy sensor 40 to be arranged in (or attached to) the extracorporeal circuit 20, since the detection of an energy transfer may then be taken as unequivocal evidence of a proper connection between the extracorporeal circuit 20 and the vascular system of the patient. It is conceivable for the energy sensor 40 to be arranged in (or attached to) the connection system C instead. In such a variant, the energy transfer no longer provides unequivocal evidence of a fluid connection between the patient and extracorporeal circuit 20, unless there is a permanent joint between the extracorporeal circuit 20 and connection system C, e.g. that the pairs of connectors C1a, C1b and C2a, C2b (FIG. 1) are permanently connected before installation in the apparatus 200, or that the tube segments 2b, 12a are directly and permanently attached to the access devices 1, 14 before installation in the apparatus 200. Alternatively, the apparatus 200 may include a dedicated safety function for ensuring proper connection of the extracorporeal circuit 20 to the connection system C, whereby an energy transfer from the patient to the connection system C may be taken as evidence of a proper connection.

For the same reason, it may be beneficial for the energy source to be arranged in (or attached to) the extracorporeal circuit 20, when the energy sensor 40 is attached to the patient. Again, the detection of an energy transfer may be taken as unequivocal evidence of a proper connection. If the energy source is arranged in (or attached to) the connection system C instead, unequivocal evidence of a proper fluid connection may require a permanent joint between the extracorporeal circuit 20 and connection system C, or the provision of the dedicated safety function.

In certain situations/applications, it may be sufficient to presume that the connection system C is properly connected to the extracorporeal circuit 20, while relying on the detection of an energy transfer between the patient and the connection system C to represent a proper connection between the extracorporeal circuit 20 and the vascular system of the patient.

The energy may pass the interface between the patient and the extracorporeal circuit 20 (and/or the connection system C) via the liquid contained in this interface, via the bulk material of the access devices 1, 14 and the tube segments, via a dedicated signal path attached to the access devices 1, 14 and the tube segments, or combinations thereof.

Below, certain embodiments will be further exemplified in relation to two specific types of energy transfers: pressure waves and electrical energy.

Pressure Waves

The pressure waves may be generated by a pulse generator of any conceivable type. A "pressure wave" is a mechanical wave in the form of a disturbance that travels or propagates through a material or substance. In the context of the following examples, the pressure waves propagate in the liquid system extending from the pulse generator to the pressure sensor, which is in direct or indirect hydrostatic contact with the liquid system. The pressure waves typically propagate in the liquid system at a velocity of about 3-20 m/s. The pressure sensor generates measurement data that forms a pressure pulse for each pressure wave. A "pressure pulse" is thus a set of data samples that define a local increase or decrease (depending on implementation) in signal magnitude within a time-dependent measurement signal ("pressure signal"). The pressure pulses appear at a rate proportional to the generation rate of the pressure waves at the pulse generator. The pressure sensor may be of any type, e.g. operating by resistive, capacitive, inductive, magnetic or optical sensing, and using one or more diaphragms, bellows, Bourdon tubes, piezo-electrical components, strain gauges, resonant wires, photo-plethysmography (PPG), accelerometers, bioimpedance, etc.

In one embodiment, which minimizes the need to add dedicated components to the patient and the apparatus 200, the pulse generator is a physiological phenomenon in the patient and the resulting pressure waves are sensed by one or more of the existing pressure sensors in the extracorporeal circuit 20.

In principle, embodiments of the invention may use pressure pulses ("physiological pulses") from any type of physiological phenomenon, be it occasional, repetitive or cyclical (i.e. periodic). However, in certain situations, it may be easier to detect a pressure pulse, or part thereof, in a series of pressure pulses originating from a repetitive or cyclical physiological phenomenon, since one pressure pulse may be used to identify another pressure pulse in the series based on an approximate, estimated or predicted temporal relation between the two pulses.

Occasional physiological phenomena include reflexes, sneezing, voluntary muscle contractions, and non-voluntary muscle contractions.

Periodic physiological phenomena include heart beats and breathing (respiration). Heart beats normally occur with a frequency of in the range of about 0.5-3 Hz, whereas breathing has a frequency of about 0.15-0.4 Hz, with frequencies typically centred around ~0.25 Hz. The present Assignee has found that the breathing of the patient causes a corresponding modulation of the pressure in the extracorporeal circuit 20, and that such a modulation may be detected by a pressure sensor in the circuit 20.

Normally, the arterial blood pressure in the subject is modulated by 4 mmHg to 6 mmHg in a wavelike manner during respiration. Deep respiration may result in blood pressure variation of 20 mmHg.

The breathing-induced modulation of the arterial blood pressure in the subject has several reasons:
- "Cross-talk" between different parts of the sympathetic control system of the brain. Signals of the respiratory centre spill over to the centre controlling the vasomotor status causing blood pressure variations, the vasomotor referring to actions upon a blood vessel which alter its diameter by contraction and dilatation.
- Breathing modulates the heart rate which modulates cardiac output and blood pressure.
- Modulation of cardiac output due to variations of the pressure in the thoracic cavity during breathing. At inspiration the left ventricle of the heart is supplied with a smaller blood volume since more blood is contained in the blood vessels in the chest at the expense of the pump volume of the heart. Blood pressure will then change as the cardiac output varies.
- Excitation of baroreceptors of the heart due to respiration. This will cause modulation of blood pressure since the sympathetic system will respond to the stretch of the baroreceptors by changing the blood pressure.
- The hydro-static pressure change due to the rise and fall of the chest during respiration of a subject in supine position. At inspiration, the centre of gravity is elevated which causes increased pressure.

In an alternative embodiment, a specific pulse generator is attached to the patient to generate the pressure waves. Such a pulse generator may be an ultrasound generator, a mechanical vibrator, a pressurized cuff, etc. Such an embodiment may further facilitate the detection of pressure pulses in the measurement data, since the approximate timing of each pressure pulse in the measurement data may be obtained from a control signal for the pulse generator, e.g. by approximating the propagation time for the pressure wave from the pulse generator to the pressure sensor.

In another embodiment, the pulse generator is a pump or a combination of pumps in the apparatus 200, and possibly other mechanical pulse generators such as valves, and the resulting pressure waves are sensed by a dedicated sensor (e.g. based on pressure measurement, PPG, bioimpedance) attached to the patient. Like in the foregoing embodiment, the detection of pressure pulses in the measurement data may be facilitated by timing data that indicates the approximate timing of each pressure pulse. Such timing data may be obtained from a pump controller (cf. 24 in FIG. 1) or a pump sensor (cf. 25 in FIG. 1).

Whenever the pressure sensor is located in (or attached to) the apparatus 200, there may be a need for removing or suppressing pressure pulses that originate from the pumps and other mechanical pulse generators in the apparatus 200 (collectively denoted "pressure artefacts" or "pump pulses" in the following). As indicated in FIG. 4 (time section A5), the pressure artefacts may dominate the measurement data and make it difficult to identify pressure pulses that originate from the pulse generator in (or attached to) the patient (collectively denoted "patient pulses" in the following). Different signal processing techniques for removal/suppression of pressure artefacts are discussed in Section V below.

If the pressure sensor is attached to the patient, a corresponding need for removal of patient pulses may arise. Although not explicitly described herein, the skilled person should have no difficulty adapting the techniques in Section V to this situation.

Electrical Energy

Measurement of electrical energy parameters is commonly used in various schemes for detecting a disconnection of a device from a patient. All of these difference schemes may also be used for detecting a connection according to embodiments of the invention. Below follows a non-limiting selection of known methods for disconnection detection based on electrical energy parameters.

WO01/47581 discloses a detection technique based on capacity coupling and earth return. Disconnection is detected as changed properties of a closed electrical loop which is formed by a capacity coupled AC generator (100 Vpp @ 35 kHz), a venous blood line, a venous needle and the patient, where the patient and the exciting device are electrically connected via earth.

U.S. Pat. No. 6,663,585 discloses a detection technique based on induction in the extracorporeal circuit. An electrical current is induced in a closed electrical loop consisting of the extracorporeal blood path and a blood vessel section between the needles. Disconnection of any needle breaks up the closed loop and may be detected with a coil placed around the blood line.

US2003/0194894 discloses a detection technique based on conductivity via galvanic contact. A galvanic contacting device is provided for the purpose of detecting access needle disconnection via conductivity measurements.

US2003/0195453 and US2003/0195454 disclose detection techniques based on various modes of electrical coupling. In US2003/0195453, methods and devices are proposed for detecting needle dislodgement based on measurement of electricity passing between the venous and arterial lines via the access. Galvanic, capacitive and inductive electrical couplings are given as alternatives. US2003/0195454 discloses a medical device capable of detecting access disconnection utilizing different kinds of electrodes. The electrodes may be connected pair-wise in different ways: to the venous and the arterial line, to either of the blood lines and to the patient. Arrangements with three electrodes and with electrodes positioned in a dialysis machine are also described. Electrical current is injected to constant value and the voltage required is measured.

US2007/0000847 discloses a detection technique based on measurement of endogenous voltages. The arterial and venous needles are electrically connected to an instrumental amplifier that passively monitors the electrical voltages produced by the patient's body and transmitted via the blood and/or conductive tubing to an alarm site.

It is realized that at least some techniques for detection of transfer of electrical energy requires an electrical connection to the patient. A electrical connection site 45 is schematically indicated in FIG. 2.

It should be noted that the foregoing description is not intended to be exhaustive. As a matter of principle, any combination of energy source and energy transfer sensor that is used, or proposed for use, now or in the future, for providing the safety function of detecting a disconnection of the connection system C, or the extracorporeal circuit 20, from the vascular system of the patient may be used to detect the establishment of a connection between the connection system C and the patient, according to embodiments of the invention.

IV. Calculation of a Parameter Value

This Section describes different embodiments for calculating the parameter value that represents the characteristic change, e.g. as part of step 306 in FIG. 3. The description is given in relation to a pressure signal acquired from a pressure sensor, but the skilled person realizes that similar embodiments are equally applicable to signals acquired from other energy transfer sensors. Furthermore, the description is focused on calculating a parameter value representing the presence of one or more patient pulses in the pressure signal. It should be understood that the description is equally applicable to the detection of other pulses in the pressure signal.

It is emphasized that the description is non-exhaustive and included for the purpose of exemplification only.

Detection of Step Change

Any known technique may be used to detect the step change in the (filtered) pressure signal caused by the connection of the extracorporeal circuit 20 to the patient. For example, the parameter value may be an individual pressure sample, a local derivative of the pressure signal, a time-average within a sliding time window in the pressure signal, etc. Low pass filtering may be applied before time-averaging, since a step change may be viewed as a change in DC level. The time-averaging may be achieved with both the mean value and the median value, depending on the assumption of the noise distribution. Another technique for detection of step change is hypothesis testing, where the step change may be modelled either as a change in DC level or a predetermined shape representing the step change.

Detection of Patient Pulse in Filtered Pressure Signal

The parameter value may be calculated based on the pressure signal after removal/suppression of the above-mentioned pressure artefacts. Such a filtered pressure signal is denoted "monitoring signal" and may be obtained via any one of the techniques described below in Section V.

To calculate the parameter value, an evaluation segment is extracted from the monitoring signal, wherein the evaluation segment represents a time window in the monitoring signal. Each evaluation segment is typically selected such that it contains or represents at least part of a patient pulse, when a fluid connection is made between the extracorporeal circuit 20 and the vascular system. The evaluation segments may be overlapping or non-overlapping in time.

Below follows different examples of the step of calculating the parameter value. The following examples fall into two different categories: frequency domain measures and time domain measures.

Frequency Domain Measures

In this variant, the evaluation segment is subjected to a frequency analysis, e.g. by Fourier analysis or an equivalent technique. The parameter value may then be calculated to represent relevant parts of the resulting energy spectrum and/or or phase angle spectrum, since at least one of these spectra may change following a connection. For example, a frequency component of the patient pulses may be detectable in the energy spectrum.

Time Domain Measures

In this variant, the parameter value is designed to represent the temporal distribution of signal values within the evaluation segment. By analyzing the temporal distribution of signal values within the evaluation segment, an improved tolerance to noise and disturbing signals may be obtained. Furthermore, compared to frequency domain measures, the use of time domain measures may provide an improved tolerance to variations in the pulse repetition interval of the patient pulses. Such variations may occur, e.g., when the patient pulses originate from a physiological phenomenon such as a human heart. Variations in heart rhythm (heart rate variability, HRV) will cause the peak from the heart in the frequency domain to be smeared out, making it harder to detect. In healthy subjects under calm conditions, HRV may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

Still further, the use of time domain measures may allow for faster detection than the use of frequency domain measures, since the former may have the ability to detect a single patient pulse (or part thereof) in the evaluation segment whereas the generation of a frequency spectrum generally benefits from a greater number of patient pulses in the evaluation segment.

The parameter value may be calculated as a statistical dispersion measure of the signal values within the evaluation segment. Non-limiting examples of potentially useful statistical dispersion measures include standard deviation ($\sigma$), variance ($\sigma^2$), coefficient of variation, (defined as standard deviation-to-mean: $\sigma/\mu$) and variance-to-mean ($\sigma^2/\mu$). Other examples include a sum of differences, e.g. given by $$\sum_{i=2}^{n} |x_i - x_{i-1}|, \text{ or } \sum_{i=1}^{n} \sum_{j=1}^{n} |x_i - x_j|.$$

or an energy measure, such as $$\sum_{i=1}^{n} x_i^2,$$

with n being the number of signal values x in the evaluation segment. Yet other examples include a measure based on a sum of absolute differences from an average value m, with the average value m being calculated for the signal values in the evaluation segment using any suitable function, such as arithmetic mean, geometric mean, median, etc. It is to be noted that all of the above suggested dispersion measures also include normalized and/or weighted variants thereof.

Instead of, or in addition to, using a statistical dispersion measure, the parameter value may result from a matching procedure, in which the evaluation segment is matched to one or more predicted signal profiles of a patient pulse. Preferably, but not necessarily, each predicted signal profile represents a single patient pulse. Typically, the matching procedure involves convolving or cross-correlating the evaluation segment and the predicted signal profile, and the parameter value is a resulting correlation value, typically the maximum correlation value.

Figure 5:
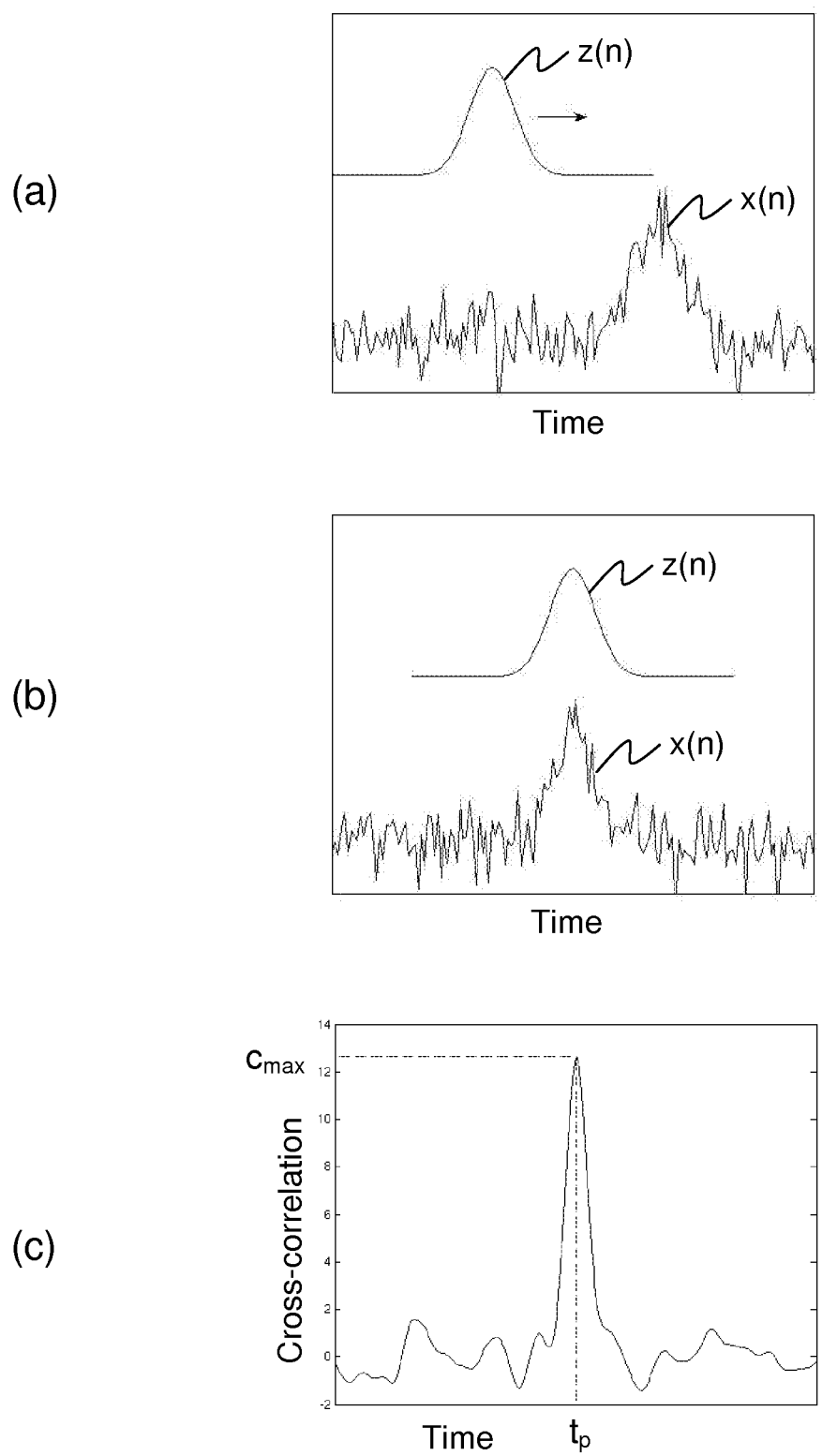
FIG. 5($a$) illustrates a matching procedure between a pressure signal segment and a predicted signal profile, FIG. 5($b$) illustrates the position of best match, and FIG. 5($c$) is a correlation curve resulting from the matching procedure in FIG. 5($a$).

FIG. 5(a) is a graph showing an example of a predicted signal profile z(n) and an evaluation segment x(n). In this particular example, the evaluation segment has a signal-to-noise ratio (SNR) of 4.8 dB. During the cross-correlation, the signal profile z(n) is slid in a number of time steps along the time axis, as indicated by an arrow in FIG. 5(a), and the integral of the product z(n)·x(n) is calculated for each time step. The cross-correlation thus results in a time sequence of correlation values, with the maximum correlation value indicating the time point of best match between x(n) and z(n). FIG. 5(b) illustrates the relative position between x(n) and z(n) at the time point for best match, and FIG. 5(c) illustrates the resulting correlation values as a function of said time steps. The magnitude of the maximum correlation value, optionally calculated as a weighted average within a range around the maximum correlation value ($c_{max}$), may thus be used as the parameter value.

The predicted signal profile may be generated as an average of a number of recordings of patient pulses. For example, it may be generated by averaging a number of evaluation segments, e.g. in a separate reference measurement. Alternatively, the predicted signal profile may be obtained by numerical simulations, or be a standard mathematical function, such as a Gaussian function, a spline function, etc.

In a variant, a statistical calculation is made based on a time-sequence of parameter values, each calculated in an iteration of the control process (FIG. 3) using another measure, such as the above-mentioned frequency domain measure or the matching measure. The statistical calculation results in an aggregate parameter value which is compared to the threshold/range in step 308. The aggregate parameter value may be calculated using any of the above statistical dispersion measures, or be calculated as an average or sum of the parameter values.

Detection of Patient Pulse in Composite Signal

The present Assignee has realized that the connection of extracorporeal circuit 20 to the vascular system of the patient may be detected without prior removal/suppression of pump pulses in the pressure signal. Instead, the parameter value is calculated from a composite signal which is acquired so as to contain both patient pulses and pump pulses, when a fluid connection is made between the extracorporeal circuit 20 and the vascular system.

Figure 6:
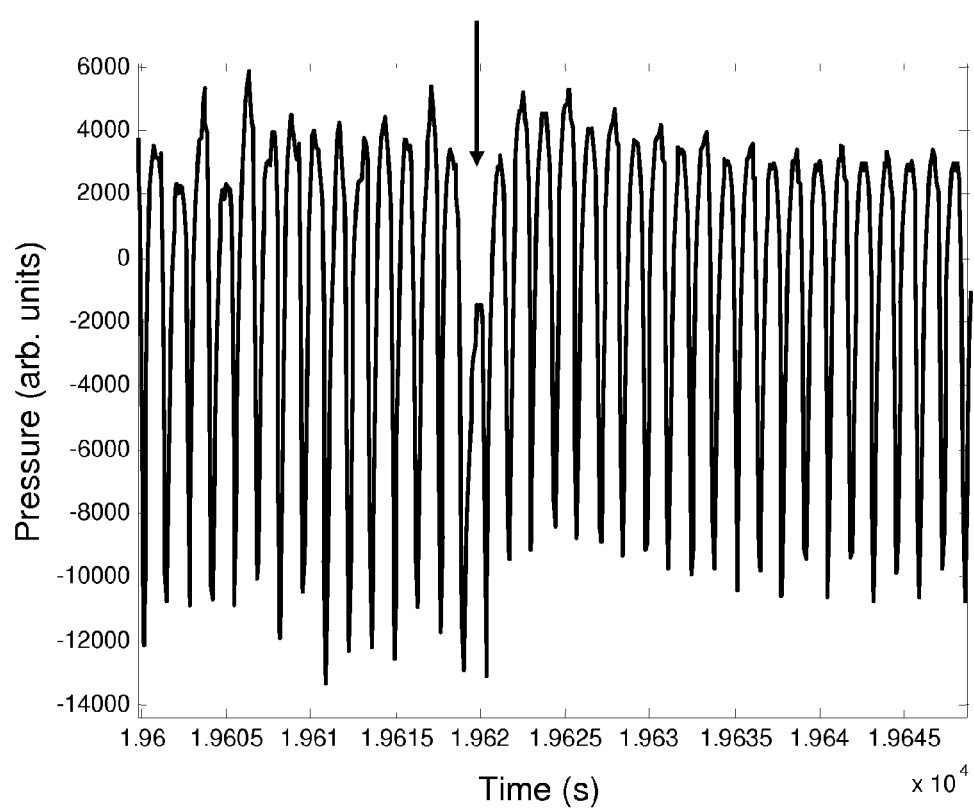
FIG. 6 is a plot of a pressure signal obtained from a sensor in the system of FIG. 1, during a disconnection of the extracorporeal blood flow circuit from the subject.

To further illustrate the underlying principle, FIG. 6 illustrates a composite signal in the form of a pressure signal from the venous sensor 4c in the extracorporeal circuit 20 of FIG. 1 during blood treatment. The arrow indicates a time of disconnection of the connection system C. A careful inspection of the composite signal reveals that that there is a change in symmetry in the composite signal before and after disconnection, specifically between pulses from consecutive revolutions/cycles of the blood pump 3.

Thus, the composite signal may be formed by the measurement data acquired from the pressure sensor, optionally pre-processed for removal of offset, high frequency noise and supply voltage disturbances, etc. It is also conceivable that such pre-processing removes specific parts of the pump pulses and/or the patient pulses. For example, it may be desirable to remove pulse components caused by switching of mechanical valves, swinging movement of tube segments, operation of a pump for dialysis fluid, etc. The pre-processing may also involve a downsampling of the measurement data.

In another implementation, the composite signal represents the envelope of the measurement data. The envelope may be given as a time-sequence of peak values extracted from the data samples (optionally after the aforesaid pre-processing). The peak values may be local maxima and/or minima, which may be identified in the measurement data by processing the time-sequence of data samples using any known technique, such as a first or second derivative test or thresholding. It may be beneficial to low-pass filter the measurement data, to remove high-frequency noise, before identifying the peak values. To further improve noise robustness, each extracted peak value may instead be calculated as an average or sum of the signal values forming each peak, e.g. including signal values within 10-25% of the peak value or within a given time range around the peak values.

In a variant, peak values may be extracted from the time-sequence of data samples based on external timing information, which indicates the timing of the pump pulses in the measurement data. For example, if the timing information indicates a time point for a pump pulse in the measurement data, the peak value may be approximated by a data sample in the measurement data at that time point, or by an average of data samples around such a time point. The timing information may e.g. be obtained from the pump sensor 25 or the pump controller 24 (see FIG. 1). Alternatively, the timing information may be calculated from measurement data acquired from the same, or another, pressure sensor in the circuit 20.

In a further variant, the envelope may be obtained by applying a linear, time-invariant filter known as a Hilbert transformer to a set of data samples (signal segment) s in the measurement data. This operation results in a transformed signal segment ŝ, which is a 90° phase-shifted version of the signal segment s. The envelope b(n) may then be derived from $b(n) = \sqrt{s^2(n) + \hat{s}^2(n)}$, with n denoting time steps in the signal segments.

For improved processing efficiency, an approximate envelope may be calculated from the signal segment s based on the relation $$\hat{b}(n) = |s(n)| + \frac{2}{\pi}|s(n+1) - s(n)|.$$

In another variant, the envelope is obtained by calculating the sum of signal values within an integration time window, which is selected to contain a plurality of signal values while being smaller than the spacing of pump pulses. By sliding the integration time window along the pressure signal, and calculating the sum for each of a number of partially overlapping integration time windows, the resulting sequence of sums will approximate the envelope of the pressure signal.

To calculate the parameter value, an evaluation segment is extracted from the composite signal, wherein the evaluation segment represents a time window in the composite signal. Each evaluation segment is typically selected such that it contains or represents at least part of a pump pulse and at least part of a patient pulse, when a fluid connection is made between the extracorporeal circuit 20 and the vascular system. The parameter value then is calculated based on the signal values within the evaluation segment.

Depending on the type of parameter, as will be exemplified below, the evaluation segment may be selected to contain/represent at least part of a patient pulse in combination with part of a pump pulse, an entire pump pulse or a plurality of pump pulses. In all embodiments, the evaluation segments may be overlapping or non-overlapping in time.

Below follows different examples of the step of calculating the parameter value. The following examples fall into four different categories: frequency domain measures, statistical measures, pulse-to-pulse symmetry measures and pump pulse matching measures. In the latter three categories, the parameter value is a time domain measure that represents the temporal distribution of signal values within the evaluation segment. Unless otherwise stated, all measures may be calculated from any one of the different types of composite signals described above.

Frequency Domain Measures

In one embodiment of the first category, the evaluation segment is subjected to a frequency analysis, e.g. by Fourier analysis or an equivalent technique. The parameter value may then be calculated to represent relevant parts of the resulting energy spectrum and/or or phase angle spectrum, since at least one of these spectra is likely to change significantly following a connection.

Statistical Measures

In one embodiment of the second category, the parameter is calculated as a statistical dispersion measure of the signal values within the evaluation segment, whereby the parameter value reflects the variation in signal amplitude within a time window in the composite signal. For suitable statistical dispersion measures, reference is made to the examples given above ("Detection of patient pulse in filtered pressure signal").

The statistical dispersion measure may alternatively be calculated to reflect the variation in pulse-to-pulse timing in the composite signal, e.g. when the composite signal is given by peak values obtained as local maxima/minima. Any one of the above-mentioned statistical dispersion measures may be used to represent such a variation in timing.

It should also be understood that an aggregate parameter value may be obtained, as exemplified in relation to the monitoring signal above, by applying a statistical calculation on a time-sequence of parameter values obtained using a measure according to the first, third and fourth categories.

Pulse-to-Pulse Symmetry Measures

In the third category, the parameter value is generated to directly reflect the pulse-to-pulse symmetry between pulses in the composite signal. In one embodiment, the parameter value is generated by comparing pairs of pulses within the evaluation segment, or between evaluation segments, with the comparison being based on a specific pulse feature. The pulse feature may e.g. relate to the peak value (amplitude), the timing or the shape of the respective pulse.

In order to calculate such a parameter value, the pulses need to be identified in the evaluation segment(s). In one embodiment, the pulses are identified based on the aforesaid timing information, such that each pulse feature is extracted at or around a time point that corresponds to a pump pulse in the evaluation segment(s). In another embodiment, the pulses are identified based on the signal values as such in the evaluation segment(s). For example, if the composite signal is made up of peak values, each peak value is already known to correspond to a pulse. Otherwise, the pulses may be identified based on local maxima/minima in the composite signal.

If the pulse feature relates to timing, the parameter value may be given by the time difference between the pairs of pulses, e.g. given by the time difference between the peaks of the pulses.

If the pulse feature relates to amplitude, the parameter value may be given by the difference in peak amplitude of the pulses, or by the ratio of the peak amplitudes of the pulses.

If the pulse feature relates to shape, the pulse feature may directly or indirectly represent the temporal signal profile of the respective pulse. In one embodiment, such a pulse feature is made up of the signal values of the pulse, or a curve fitted to the signal values, and is thus a temporal representation of the actual shape of the pulse. The skilled person realizes that the parameter value may be formed by any known similarity measure (or equivalently, difference measure), including a correlation value between the temporal representations, a sum of differences between mutually aligned signal values in the temporal representations, and any suitable $L^n$-norm evaluated based on these differences, such as an $L^1$-norm (sum of absolute differences, aka Manhattan norm) or an $L^2$-norm (Euclidian norm). For calculation of the similarity measure, the temporal representations of the two pulses may need to be aligned temporally, which may be achieved by using the aforesaid timing information which is indicative of the timing of the pump pulses. The comparison of shape-related pulse features may or may not include an "autoscaling" between the temporal representations, in which the magnitude of one is adapted to the magnitude of the other, e.g. by minimizing a measure of the difference between the temporal representations, as is well-known in the art.

Figure 7:
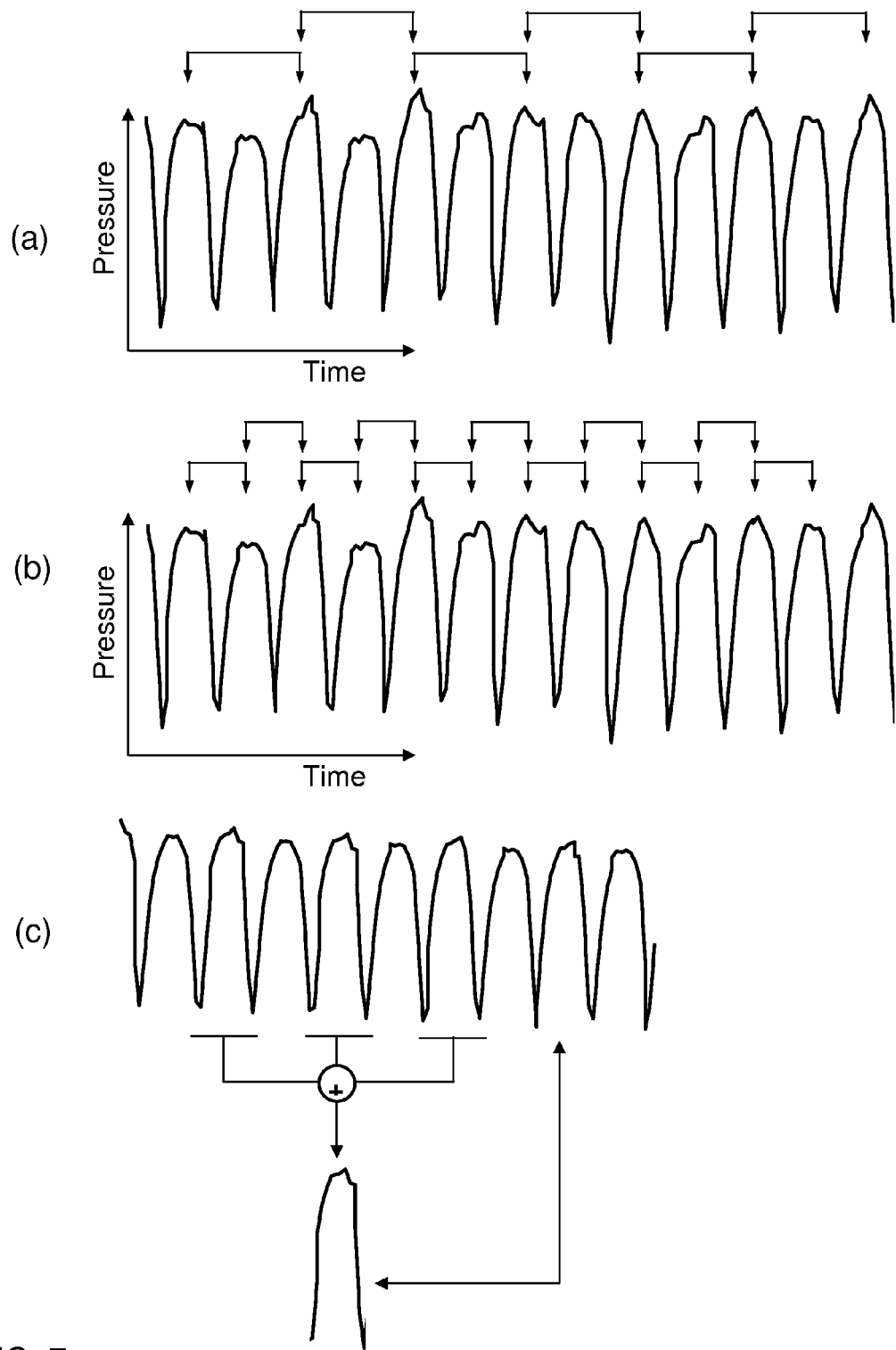
FIGS. 7($a$)-($c$) are plots of pressure signals to illustrate calculation of pulse-to-pulse symmetry measures.

Irrespective of the type of pulse feature, the comparison may be made between pulses that are known to be essentially identical, at least on average, in the absence of disturbances. In the example of a peristaltic pump, which generates a set of unique pulses for each revolution of its rotor, this may involve comparing corresponding pulses for different revolutions of the rotor. FIG. 7(a) includes part of the composite signal in FIG. 6 and indicates, by double-ended arrows, that pairs of pulses are formed by every second pulse. In the illustrated example, the peristaltic pump generates a sequence of two unique pressure pulses P1, P2 (see FIG. 8 and related discussion below) for each revolution, and comparison is made between pulses in the composite signal that correspond to either P1 pulses or P2 pulses. When shape features are compared, however, it is also conceivable to compare groups of unique pulses with each other. In the example of FIG. 7(a), such a group may be formed by a consecutive pair of P1 and P2 pulses.

Alternatively, the comparison may be made for pulses that have another known average relation to each other, in the absence of disturbances. FIG. 7(b) includes part of the composite signal in FIG. 6 and indicates, by double-ended arrows, that pairs of pulses are formed by consecutive pulses. In the illustrated example, the comparison is made between P1 and P2 pulses.

In a variant, the parameter value may be calculated by comparing pulse features for pairs of pulses within the composite signal, and by aggregating the results of the individual comparisons. For example, the parameter value may be generated by evaluating any of the above-mentioned statistical dispersion measures on the results, or by calculating the average or sum of the results.

In a variant, the pulse feature is extracted from the evaluation segment and compared with a time average of a corresponding pulse feature obtained from one or more preceding pulses within the same evaluation segment, or in one or more preceding evaluation segments. The pulse feature may be any one of peak amplitude, timing and shape. FIG. 7(c) illustrates an example involving a shape feature. Here, the time average of the pulse shape is calculated by combining (e.g. by temporally aligning and summing) three temporal representations of preceding pulses based on the aforesaid timing information. Then, the parameter value is calculated by comparing a current pulse shape in the composite signal with the time average. It is to be understood that the selection of every second pulse in FIG. 7(c) is merely intended as an example, and also that the time average may be formed by combining any number of temporal representations. It may also be noted that the evaluation of the parameter value may differ depending on the relation between the rate of pump pulses and the rate of patient pulses in the composite signal. For example, in relation to the example of FIG. 7(c), if the patient pulses are known to have a fixed (synchronous) timing in relation to the pump pulses, the time average will approximate the combined shape of a pump pulse and a patient pulse. Thus, a similarity between the current pulse shape and the time average indicates a connection between the extracorporeal circuit 20 and the patient. If the patient pulses are not synchronous with the pump pulses, the time average will approximate the shape of a pump pulse, and a similarity between the current pulse shape and the time average will indicate a lack of connection between the extracorporeal circuit 20 and the patient.

Pump Pulse Matching Measures

In the fourth category, the parameter value is generated in a matching procedure, in which shape data is extracted from the composite signal, which may be a pressure signal or an envelope as described in the foregoing. In the following, it is assumed that the composite signal is a pressure signal, and that the shape data is matched to predicted shape data for a pump pulse. If the pump generates more than one unique pump pulse, the predicted shape data may, but need not, represent a complete set of unique pump pulses.

The shape data may directly or indirectly represent the temporal signal profile of one or more pulses in the evaluation segment. In one embodiment, the shape data is made up of all or a subset of the signal values in the evaluation segment, and is thus a temporal representation of the actual shape of at least part of a pulse in the evaluation segment (denoted "temporal shape data"). The temporal shape data may or may not be a downsampled version of the evaluation segment.

The identification of pulses in the evaluation segment may be done as described above in relation to pulse-to-pulse symmetry measures.

Figure 8:
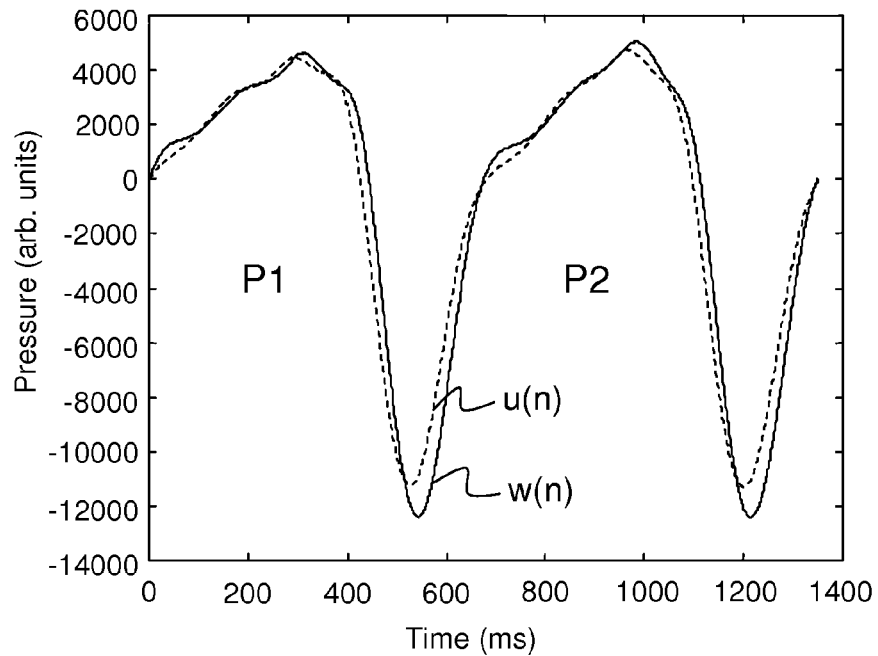
FIG. 8 is a plot of temporal shape data obtained from a pressure signal and a corresponding predicted signal profile of two consecutive pump pulses.

FIG. 8 illustrates temporal shape data w(n) obtained from an evaluation segment generated based on measurement data from the venous sensor 4c in the extracorporeal circuit 20 of FIG. 1. In this example, the temporal shape data w(n) comprises two pressure pulses P1, P2, which are generated by a respective roller in the blood pump engaging a tubing segment in the peristaltic blood pump (cf. rollers 3a and 3b in FIG. 1). FIG. 8 also illustrates a predicted signal profile u(n) which represents the shape of the pump pulses P1, P2.

In another embodiment, the shape data is made up of spectral shape data, such as signal amplitude given as a function of frequency and/or signal phase given as a function of frequency. Such spectral shape data may be obtained by spectral analysis of the evaluation segment, e.g. via Fourier analysis or any equivalent technique. It should be noted that a complete representation of the shape of the evaluation segment would require the spectral shape data to include both the frequency distribution in amplitude and the frequency distribution in phase. In the context of the present application, however, either one of these frequency distributions is deemed to represent the shape of the evaluation segment and may thus be used to calculate the parameter value, by comparing the frequency distribution to a corresponding predicted signal profile, which is given as a frequency distribution of signal amplitude or phase, as applicable (cf. FIGS. 15(a)-15(d) below).

The parameter value may represent the similarity or dissimilarity between the temporal or spectral shape data and one or more corresponding predicted signal profiles. The parameter value may thus be derived by comparing or matching the shape data to the predicted signal profile(s). If two predicted signal profiles are used, one may represent a connection and one may represent a disconnection between the circuit 20 and the patient. The comparing/matching may thus result in two parameter values, which may be evaluated collectively (in step 308). Although the following description assumes that only one predicted signal profile is used, it is equally applicable to the use of two predicted signal profiles.

In one embodiment, using temporal shape data, the parameter value is obtained by convolving or cross-correlating the temporal shape data w(n) and the predicted signal profile u(n), with the parameter value being given by a resulting correlation value, typically the maximum correlation value.

In another embodiment, using temporal shape data, the temporal shape data w(n) and the predicted signal profile u(n) are aligned with each other, such that the pulse(s) in the shape data and the predicted signal profile overlap (e.g. as shown in FIG. 8), based on timing information which indicates the timing of the pump pulse(s) in the temporal shape data w(n). Such timing information may alternatively be implicit, e.g. if each evaluation segment is generated with known timing with respect to the pump pulses. In such a variant, the temporal shape data may be extracted and directly aligned with the predicted signal profile.

In an embodiment using the above-mentioned spectral shape data, spectral shape data may be directly aligned with a corresponding predicted signal profile, since both the spectral shape data and the predicted signal profile may be given within a known range of frequencies.

The comparing/matching process may or may not include an "autoscaling" between the shape data and the predicted signal profile, in which the magnitude of one is adapted to the magnitude of the other, e.g. by minimizing a measure of the difference between the shape data and the predicted signal profile, as is well-known in the art.

The parameter value may be calculated as a correlation value, a sum of differences between mutually aligned signal values in the shape data and the predicted signal profile, or any suitable $L^n$-norm evaluated based on these differences, such as an $L^1$-norm (sum of absolute differences, aka Manhattan norm) or an $L^2$-norm (Euclidian norm). The skilled person realizes that any known difference or similarity measure may be evaluated and used as parameter value indicative of the shape of the pump pulse(s).

It should be understood, though, that the temporal shape data may include a larger number of pulses than the predicted signal profile, whereby each temporal shape data may be matched against several predicted signal profiles, which may or may not be identical. For example, when the blood pump has a number of different pump strokes, each generating a unique pump pulse (cf. P1, P2 in FIG. 8), the temporal shape data may be matched against a set of predicted signal profiles representing the different pump pulses.

The above-described embodiments rely on the use of a predicted signal profile (temporal or spectral) that properly represents the temporal profile of the pump pulse(s). The predicted signal profile may be obtained in a reference measurement, based on measurement data acquired from one or more of the pressure sensors 4a-4c in the circuit 20, suitably by identifying and possibly averaging a set of pump pulses in the measurement data. During the reference measurement, the patient pulses are either prevented from reaching the relevant pressure sensor, or they are removed by proper filtering of the measurement data. In another variant, the reference measurement may operate on measurement data from a pressure sensor which is substantially isolated from the patient pulses. In such a situation, the measurement data may be obtained from the isolated sensor, and used for generating the predicted signal profile (optionally after adjustment/modification for differences in confounding factors, see below), which is then used in the actual monitoring process. For example, the pressure signal from the system sensor 4b in the extracorporeal circuit 20 of FIG. 1 may be essentially isolated from the patient pulses, and this pressure signal may thus be used in a reference measurement, while the actual monitoring process may operate on measurement data from either of the pressure sensors 4a-4c.

Alternatively, a predetermined (i.e. predefined) signal profile may be used, which optionally may be modified according to a mathematical model accounting for wear in the blood pump, blood flow rates, tubing dimensions, speed of sound in the blood, etc, to generate the predicted signal profile.

Different embodiments for predicting or estimating the pump signal profile in the extracorporeal circuit 20 of FIG. 1 are further described in Section VI below.

The above-described matching procedure may also be used when the composite signal is a envelope obtained from the pressure signal, wherein the extracted shape data is matched to a predicted signal profile (temporal or spectral) for the envelope (i.e. an "envelope reference profile"). Although Section VI describes techniques for obtaining predicted signal profiles for pressure signals, the skilled person should have no difficulty to derive an envelope reference profile by applying the techniques in Section VI. For example, the temporal predicted signal profile obtained in Section VI may be processed for envelope extraction and then used as an envelope reference profile. In another embodiment, the envelope reference profile is given by a sinusoid with a frequency of $0.5f_0$, or a multiple thereof.

V. Signal Processing and System Control in Relation to a Pressure Signal

This Section describes different techniques for removing/suppressing pump pulses in a pressure signal obtained by sampling measurement data from a pressure sensor in an apparatus such as the dialysis machine in FIG. 1. Although the techniques are described in relation to patient pulses originating from a physiological phenomenon in the patient ("physiological pulses"), corresponding techniques may be used to isolate other types of patient pulses.

Figure 9:
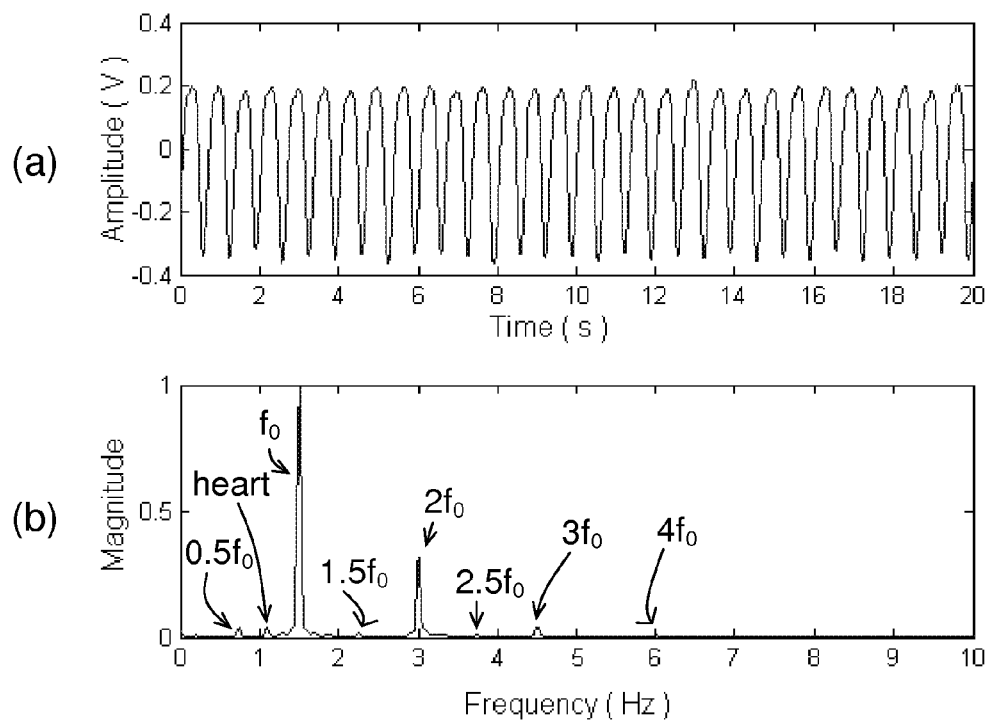
FIG. 9($a$) is a plot in the time domain of a pressure signal containing both pump frequency components and a heart signal, and FIG. 9($b$) is a plot of the corresponding signal in the frequency domain.

FIG. 9(a) shows an example of a pressure signal in the time domain, and FIG. 9(b) shows the corresponding energy spectral density, i.e. signal amplitude as a function of frequency. The energy spectral density reveals that the detected pressure signal contains a number of different frequency components emanating from the blood pump (3 in FIG. 1). In the illustrated example, there is a frequency component at the base frequency ($f_0$) of the blood pump (at 1.5 Hz in this example), as well as its harmonics $2f_0$, $3f_0$ and $4f_0$. The base frequency, also denoted pumping frequency in the following, is the frequency of the pump strokes that generate pressure waves in the extracorporeal circuit 20. For example, in a peristaltic pump of the type shown in FIG. 1, two pump strokes are generated for each full revolution of the rotor 3', i.e. one pump stroke for each roller 3a, 3b. FIG. 9(b) also indicates the presence of a frequency component at half the pumping frequency ($0.5f_0$) and harmonics thereof, in this example at least $f_0$, $1.5f_0$, $2f_0$ and $2.5f_0$. FIG. 9(b) also shows a heart signal (at 1.1 Hz) which in this example is approximately 40 times weaker than the blood pump signal at the base frequency $f_0$. Although not shown in FIG. 9, the pressure signal may also contain signal components originating from other mechanical pulse generators (not shown) in the circuit 20, such a valves, a pump for dialysis fluid, etc.

Figure 10:
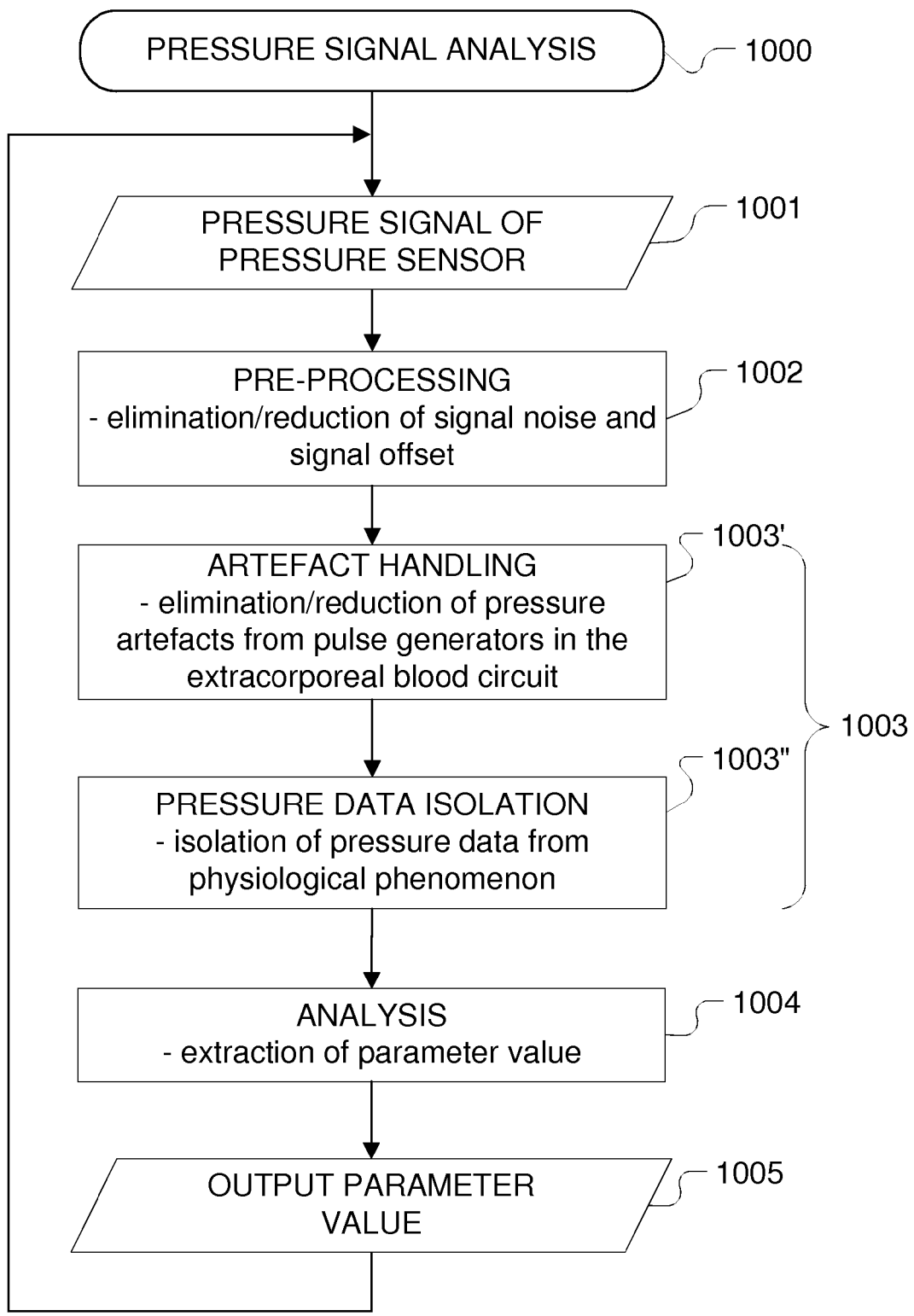
FIG. 10 is a flow chart of a process for signal analysis of a pressure signal obtained in the system configuration of FIG. 1.

FIG. 10 is a flow chart that illustrates steps of a signal analysis process 1000 according to an embodiment of the present invention. It is initiated by acquiring a pressure signal, step 1001, e.g. from the venous or the arterial pressure sensor. The signal analysis process may be divided into a number of main steps: a pre-processing step 1002, a signal extraction step 1003 and an analysis step 1004. The pre-processing step 1002 includes elimination or reduction of undesired signal components, such as offset, high frequency noise and supply voltage disturbances. The signal extraction step 1003 may conceptually be separated into two sub-steps: an elimination or reduction of pressure artefacts originating from pulse generators in (or associated with) the extracorporeal circuit (step 1003') and a step of isolating pressure data originating from a relevant physiological phenomenon (step 1003"). Generally, more than one physiological phenomenon in the patient may give rise to pressure pulses in the pressure signal. Such physiological phenomena include the heart, the breathing system, the autonomous system for blood pressure regulation and the autonomous system for body temperature regulation. In certain situations, it may be desirable to process the pressure signal for isolation of pressure pulses originating from a specific one of the physiological phenomena.

The signal extraction step 1003 denotes a process of generating a time-dependent signal (also denoted "monitoring signal" herein) which is free or substantially free from unwanted pressure modulations. It should be noted that the steps 1002, 1003', 1003" may be executed in any order, and also that the functionality of one step may be included in another step. For example, all or part of the elimination of signal noise and signal offset (i.e. step 1002), as well as all or part of the elimination of pressure artefacts (step 1003'), may be included in the algorithms for pressure data isolation (step 1003"). For instance, the pressure signal may be band-pass filtered or low-pass filtered to isolate a breathing signal, in a way such that signal noise and/or signal offset and/or pressure artefacts are eliminated from the pressure signal. Furthermore, any of steps 1002, 1003' and 1003" may be omitted, depending on the amount of signal interference and the required quality of the resulting monitoring signal.

In the analysis step 1004, a dedicated signal analysis algorithm is applied for extraction of a parameter value, e.g. as described in Section IV above. In step 1005, the parameter value is output, for use in determining whether a characteristic change has occurred, e.g. according to step 308 in FIG. 3.

Figure 11:
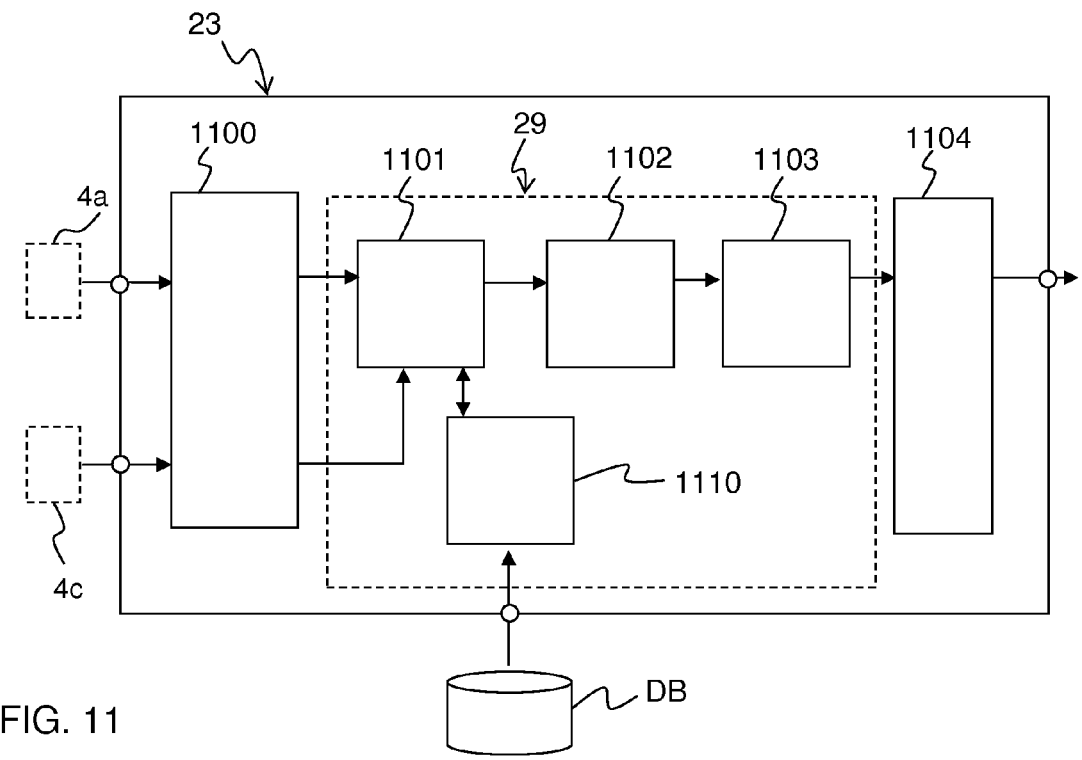
FIG. 11 is a block diagram of a device for controlling the system in FIG. 1.

FIG. 11 is a block diagram to illustrate an embodiment of the main controller 23 (FIG. 1). The main controller 23 includes an input or data acquisition part 1100 which is configured to acquire pressure data from the arterial sensor 4a and the venous sensor 4c, and generate a respective input signal for the data analysis part 29. The data analysis part 29 includes a signal analysis block 1101 which receives the input signals and implements step 306 in FIG. 3, e.g. embodied as the signal analysis process in FIG. 10. The data analysis part 29 also comprises a decision block 1102 which receives the parameter values (one for the arterial signal and one for the venous signal) calculated by block 1101 and which implements step 308 in FIG. 3 to determine if a characteristic change has occurred. The main controller 23 further includes an action controller block 1103 that decides on an appropriate action to be taken if block 1102 signals that the characteristic change has occurred. The action is represented by one or more control signals that are output by block 1103 via an output part 1104. It should be understood that the parts 1100 and 1104 may form part of the I/O part 28 in FIG. 1.

In FIG. 11, the data analysis part 29 also includes a pulse prediction block 1110 which implements a step for obtaining a pulse profile which is a predicted temporal profile of pressure artefacts (pump pulses) generated in the extracorporeal circuit 20. The pulse prediction block 1110 may operate on data from a database DB (a reference library). The resulting pulse profile may be provided to block 1101 and used for time domain filtering of the pressure signals, as will be explained in detail below. The functionality of block 1110 is further exemplified in Section VI below. In a variant (not shown), the pulse profile may instead be provided to block 1102 for use in calculating one of the above-described "pump pulse matching measures".

The data analysis part 29, and thus blocks 1101-1103 and 1110, may be implemented by software instructions that are executed by a processing device, such as a general- or special-purpose computer device or a programmed microprocessor. However, it is conceivable that some or all blocks are fully or partially implemented by dedicated hardware, such as an FPGA, an ASIC, or an assembly of discrete electronic components (resistors, capacitors, operational amplifier, transistors, filters, etc), as is well-known in the art.

In the following, different embodiments of the signal extraction step 1003, and thus part of the functionality in block 1101, will be exemplified and described in further detail.

Elimination of Artifacts (Step 1003')

In the simplest case, no pump or other source of pressure artefacts is active in the extracorporeal circuit 20 during the data acquisition. For instance, the blood pump 3 may have been shut down. In such a case, step 1003' may be omitted.

In the general case, however, one or more pumps are running or other sources of cyclic or non-cyclic, repetitive or non-repetitive artefacts are present in the input signal to step 1003'/block 1101. Information on cyclic disturbances may be known from external sources, e.g. other sensors (e.g. the pump sensor 25 in FIG. 1), or may be estimated or reconstructed from system parameters.

Cyclic pressure artefacts may originate from operating one or more blood pumps, and further pumps such as pumps for dialysis fluid, repetitive actuation of valves, and movements of membranes in balancing chambers. According to the findings in connection with the present invention, artefacts may also originate from mechanical resonance of system components such as swinging movements of bloodlines energized by e.g. a pump. Frequencies of bloodline movements are given by the tube lengths and harmonics thereof and by the beating between any frequencies involved, i.e. between different self-oscillations and pump frequencies. These frequencies may differ between the venous and arterial lines. Mechanical fixation of the bloodlines and other free components may remedy the problem of mechanical resonance. Alternatively, an operator may be instructed to touch or jolt the blood lines to identify natural frequencies associated with the blood lines, which information may be used in the analysis for improved removal of components not belonging to the pressure data of interest.

Examples of non-cyclic artefacts are subject movement, valve actuation, movements of tubings, etc.

Elimination of artefacts may, e.g., be provided by any or a combination of:
  Controlling a pulse generator in the extracorporeal fluid system, such as a pump
    By temporarily shutting down the pulse generator;
    Shifting the pulse generator frequency;
  Low pass, band pass or high pass filtering;
  Spectral analysis and filtering in the frequency domain;
  Time domain filtering.

Controlling a Pulse Generator

Artifacts from a pulse generator, such as a pump, in the extracorporeal circuit may be avoided by temporarily shutting down (disabling) the pulse generator, or by shifting the frequency of the pulse generator away from frequencies of the relevant physiological phenomenon.

A feedback control with respect to the physiological phenomenon, e.g. based on an output signal of a pulse sensor on the patient, may be used to set the pump frequency optimally for detection of pressure pulses originating from the physiological phenomenon. Hence, pump controller 24 of FIG. 1 may set the pump frequency so as to facilitate the detection of the relevant pressure pulses, i.e. the pump frequency is controlled to minimize any overlap in frequency between the pump pulses and the patient pulses. For example, the pump frequency may be periodically increased and decreased around the overlap frequency, so as to maintain the overall blood flow rate.

Applying Low Pass, Band Pass or High Pass Filters

The input signal to step 1003'/block 1101 may be fed into a filter, e.g. digital or analog, with frequency characteristics, such as frequency range and/or centre of frequency range, matched to the frequencies generated by a pulse generator, such as the blood pump 3 (FIG. 1), in the extracorporeal circuit. For instance, in a case where the blood pump operates within the frequency range of 1 Hz, a suitable low pass filter may be applied in order to remove pressure artefacts above 1 Hz while retaining frequency components of a physiological phenomenon below 1 Hz. Correspondingly, a high pass filter may be applied to retain frequency components of a physiological phenomenon above a frequency of the pulse generator. Alternatively, one or more bandstop filters, notch filters or the like may be utilised to remove/attenuate frequencies in one or more confined ranges.

Spectral Analysis and Filtering in the Frequency Domain

The input signal to step 1003'/block 1101 may be subjected to spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person.

Time Domain Filtering

Artifact elimination by filtering in the time domain is further disclosed and exemplified in Sections VI and VII below. In addition to these Sections VI and VII, reference is also made to WO2009/156175, which is incorporated herein in its entirety by this reference.

By filtering the pressure signal in the time-domain, it is possible to essentially eliminate artefacts, even if the artefacts and patient pulses overlap or nearly overlap in the frequency domain, and even if the patient pulses are much smaller in amplitude than the artefacts. By "essentially eliminating" is meant that the artefacts are removed from the pressure signal to such an extent that the patient pulses may be detected and analysed for the purpose of identifying the characteristic change.

A frequency overlap is not unlikely, e.g. if one or both of the artefacts and the patient pulses is made up of a combination of frequencies or frequency ranges.

Furthermore, the frequency, amplitude and phase content of the artefacts and the patient pulses may vary over time. For example, such variations (HRV) are known to occur in the heart rhythm, as discussed in Section IV above.

Any frequency overlap may make it impossible or at least difficult to remove artefacts by conventional filtering in the frequency domain. Furthermore, frequency variations may make it even harder to successfully remove artefacts, since the frequency overlap may vary over time. Even in the absence of any frequency overlap, frequency variations may make it difficult to define filters in the frequency domain.

Still further, the time domain filtering may make it possible to remove artefacts for individual patient pulses, and may thus improve the response time compared to filtering in the frequency domain, which may need to operate on a sequence of artefacts and patient pulses in the pressure signal.

Isolation of Pressure Data from a Physiological Phenomenon (Step 1003")

Isolating pressure data originating from a relevant physiological phenomenon may be provided by any or a combination of:

Low pass, band pass or high pass filtering;
Spectral analysis and filtering in the frequency domain;
Time domain filtering.

Applying Low Pass, Band Pass or High Pass Filters

The input signal to step 1003"/block 1101 may be fed into a filter, e.g. digital or analog, with frequency characteristics, such as frequency range and/or centre of frequency range, matched to the frequencies of a signal of relevant physiological phenomenon where e.g. in case the isolation concerns:

Breathing, a frequency range of about 0.15-0.4 Hz may be allowed to pass the filter;
Heart, a frequency range of about 0.5-3 Hz may be allowed to pass the filter.

The filter may include one or more of a low pass filter, a band pass filter, a high pass filter, a bandstop filter, a notch filter and other similar or equivalent filters.

According to an alternative, the main controller 23 is configured to set the cut-off frequency or frequencies of the filter, at least in part, based on patient-specific information, i.e. existing data records for the patient, e.g. obtained in earlier treatments of the same patient. The patient-specific information may be stored in an internal memory of the apparatus 200, on an external memory which is made accessible to the apparatus 200, or on a patient card where the information is e.g. transmitted wirelessly to the apparatus 200, e.g. by RFID (Radio Frequency IDentification).

Spectral Analysis and Filtering in the Frequency Domain

The input signal to step 1003"/block 1101 may be subjected to spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person.

Time Domain Filtering

Pressure data originating from a specific physiological phenomenon may be extracted as an error signal of an adaptive filter. The adaptive filter is fed with both the input signal and a predicted signal profile of a cyclic disturbance. The cyclic disturbance may be pressure pulses from any of the other physiological phenomena (e.g. heart or breathing). Particularly, a reconstructed pressure profile originating from the heart or the breathing system of the patient may be input to the adaptive filter. This and other time domain filtering techniques for removing unwanted signal components from a measurement signal is further disclosed and exemplified in Section VII below. Although Section VII is concerned with eliminating pressure artefacts originating from a pulse generator in an extracorporeal circuit, such as a blood pump, it is equally applicable for eliminating heart or breathing pulses originating from unwanted physiological phenomena, as long as it is possible to obtain a predicted signal profile of the heart or breathing pulses (also denoted "predicted physiological profile" in Section VII). The skilled person realizes that such a predicted signal profile may be obtained in ways equivalent to those described in Section VI below. Such ways include using a signal profile which is fixed and predetermined, e.g. by simulation or reference measurement, using a signal profile which is intermittently updated based on reference measurements, using a signal profile which is obtained from a reference library based on one or more current system parameter values, and using a signal profile which is obtained by modifying a predetermined profile based on one or more current system parameter values. The system parameter values may relate to a rate of heart/breathing pulses, which may be derived from a dedicated sensor in the extracorporeal circuit or on the patient or from one of the pressure sensors 4a-4c, and/or one or more of the system parameters listed in Section VI.

VI. Obtaining a Predicted Signal Profile of Pump Pulses

This Section describes different embodiments for predicting or estimating the signal profile of pump pulses in a pressure signal obtained from one or the pressure sensors 4a-4c in the extracorporeal circuit 20. The predicted signal profile is typically given as a series of pressure values over a period of time normally corresponding to at least one complete pump cycle (pump stroke) of the blood pump 3.

Returning to FIG. 8, it illustrates an example of a predicted signal profile u(n) for the system in FIG. 1. Since the blood pump 3 is a peristaltic pump, in which two rollers 3a, 3b engage a tube segment during a full revolution of the rotor 3', the pressure profile consists of two pump strokes. The pump strokes may result in different pressure values (pump profiles P1, P2), e.g. due to slight differences in the engagement between the rollers 3a, 3b and the tube segment, and thus it may be desirable for the predicted signal profile to represent both pump strokes. If a lower accuracy of the predicted signal profile may be tolerated, e.g. if the output of the subsequent process (e.g. the pump pulse matching process in Section V or the removal process in Section VII) is acceptable, the predicted signal profile might represent one pump stroke only.

On a general level, the predicted signal profile may be obtained in a reference measurement, through mathematical simulation of the fluid system, or combinations thereof.

Reference Measurement

A first main group of methods for obtaining the predicted signal profile is based on deriving a time-dependent reference pressure signal ("reference signal") from a pressure sensor in the system, typically (but not necessarily) from the same pressure sensor that provides the measurement signal (pressure signal) that is to be processed for removal of pump pulses. During this reference measurement, the patient pulses are prevented from reaching the relevant pressure sensor, e.g. by isolating the pressure sensor from the pulse waves generated in the patient. For example, the reference measurement may be carried out during a priming phase, in which the extracorporeal circuit 20 is detached from the patient and a priming fluid is pumped through the blood lines. Alternatively, the reference measurement may be carried out in a simulated treatment with blood or any other fluid. Optionally, the reference measurement may involve averaging a plurality of pump pulses to reduce noise. For example, a plurality of relevant signal segments may be identified in the reference signal, whereupon these segments are aligned to achieve a proper overlap of the pump pulses in the different segments and then added together. The identifying of relevant signal segments may be at least partially based on timing information which indicates the expected position of each pump pulse in the reference signal. The timing information may be obtained from a trigger point in the output signal of the pump sensor 25, in a control signal of the pump controller 24, or in the pressure signal from another one of the pressure sensors 4a-4c. For example, a predicted time point of a pump pulse in the reference signal may be calculated based on a known time delay between the trigger point and the pressure sensor that generates the reference signal. In variant, if the pump pulses are periodic, relevant signal segments may be identified by identifying crossing points between the reference signal and a given signal level, wherein the relevant signal segments are identified to extend between any respective pairs of crossing points.

In a first embodiment, the predicted signal profile is directly obtained in a reference measurement before the extracorporeal circuit 20 is connected to the patient, and is then used as input to the subsequent removal process, which is executed during the monitoring process (e.g. the control process in FIG. 3). In this embodiment, it is thus assumed that the predicted signal profile is representative of the pump pulses also when the extracorporeal circuit 20 is connected to the patient. Suitably, the same pump frequency/speed is used during the reference measurement and during the monitoring process. It is also desirable that other relevant system parameters are maintained essentially constant.

Figure 12:
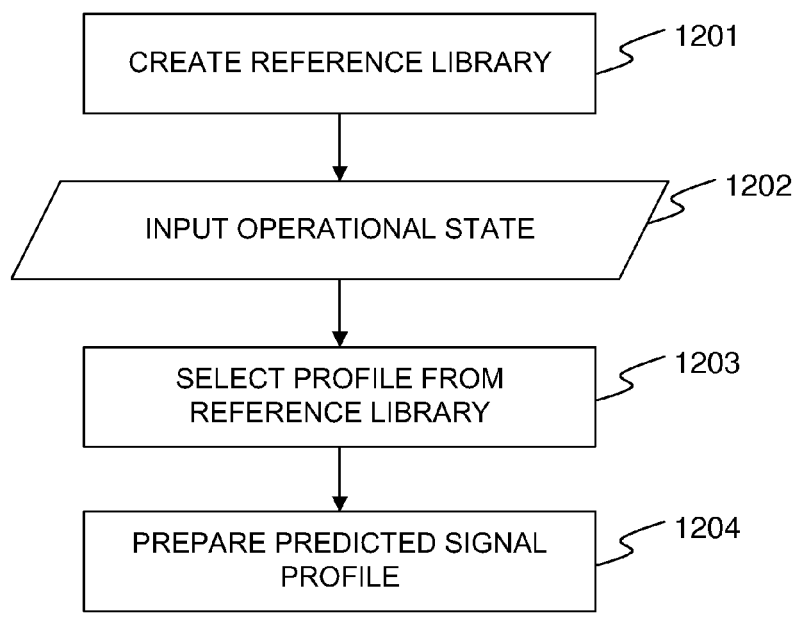
FIG. 12 is a flow chart of a process for obtaining a predicted signal profile.

FIG. 12 is a flow chart of a second embodiment. In the second embodiment, a reference library or database is first created based on the reference measurement (step 1201). The resulting reference library is typically stored in a memory unit, e.g. RAM, ROM, EPROM, HDD, Flash, etc (cf. DB in FIG. 11) in the apparatus 200. During the reference measurement, reference pressure signals are acquired for a number of different operational states of the extracorporeal circuit. Each operational state is represented by a unique combination of system parameter values. For each operational state, a reference profile is generated to represent the signal profile of the pump pulses. The reference profiles together with associated system parameter values are then stored in the reference library, which is implemented as a searchable data structure, such as a list, look-up table, search tree, etc.

During the actual monitoring process, i.e. when pump pulses are to be eliminated from the pressure signal, current state information indicating the current operational state of the extracorporeal circuit 20 is obtained from the system, e.g. from the pump sensor 25, the pump controller 24 or otherwise (step 1202). The current state information may include a current value of one or more system parameters. The current value is then matched against the system parameter values in the reference library. Based on the matching, one or more reference profiles are selected (step 1203) and used for preparing the predicted signal profile (step 1204).

Generally, the aforesaid system parameters represent the overall system state, including but not limited to the structure, settings, status and variables of the apparatus 200 or its components. In the system of FIG. 1, exemplary system parameters may include:

Pump-related parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc Dialysis machine settings: temperature, ultrafiltration rate, mode changes, valve position/changes, etc Disposable dialysis equipment/material: information on pump chamber/pump segment (material, geometry and wear status), type of blood line (material and geometry), type of dialyser, type and geometry of access devices, etc Dialysis system variables: actual absolute pressures of the system upstream and downstream of the blood pump, e.g. venous pressure (from sensor 4c), arterial pressure (from sensor 4a) and system pressure (from sensor 4b), gas volumes trapped in the flow path, blood line suspension, fluid type (e.g. blood or dialysis fluid), etc Patient status: blood access properties, blood properties such as e.g. hematocrit, plasma protein concentration, etc It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the extracorporeal circuit 20 during the monitoring process. In other words, the pump frequency is used as search variable in the reference library. The pump frequency may e.g. be given by a set value for the blood flow rate output from the pump controller 24, or by an output signal of the pump sensor 25. Alternatively, the pump frequency may be obtained by frequency analysis of the pressure signal from any of the sensors 4a-4c (FIG. 1). Such frequency analysis may be achieved by applying any form of harmonics analysis to the pressure signal, such as Fourier or wavelet analysis. As indicated in FIG. 9(b), the base frequency $f_0$ of the pump may be identified in a resulting power spectrum.

In the following, three examples are given of techniques for generating the predicted signal profile by accessing such a reference library.

Figure 13:
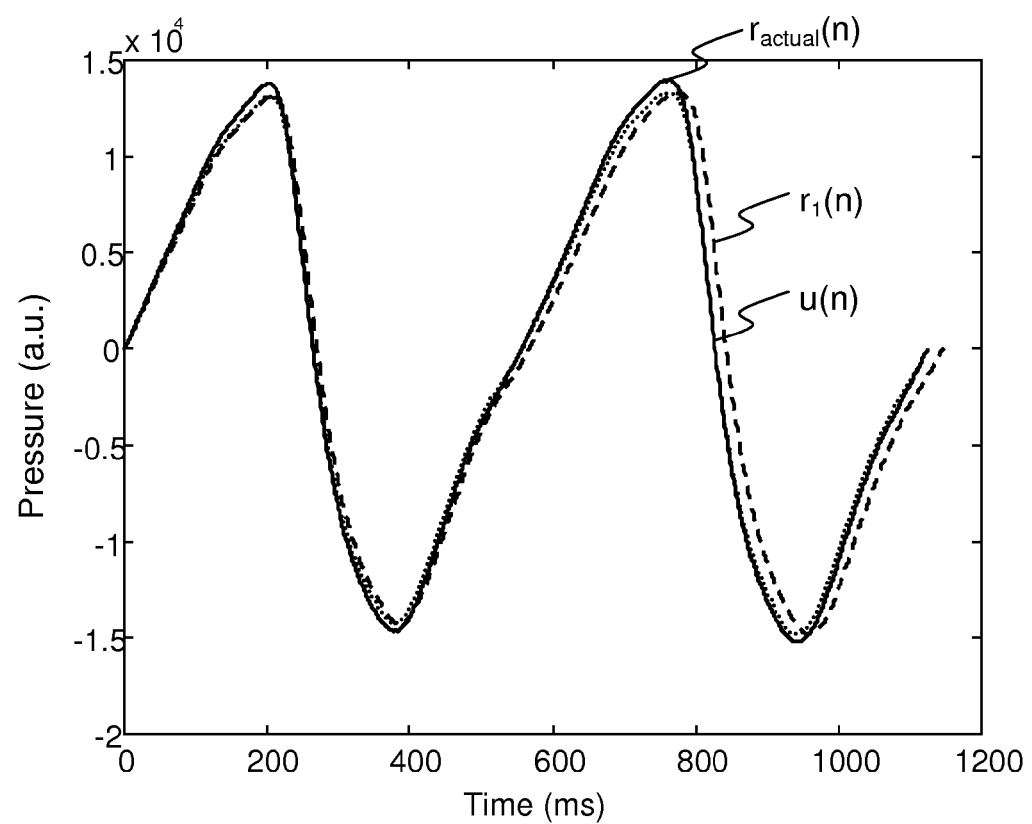
FIG. 13 is a plot to illustrate an extrapolation process for generating a predicted signal profile.

In a first example, the reference profiles stored in the reference library are temporal profiles. The reference library is searched for retrieval of the reference profile that is associated with the pump frequency that lies closest to the current pump frequency. If no exact match is found to the current pump frequency, an extrapolation process is executed to generate the predicted signal profile. In the extrapolation process, the retrieved reference profile is scaled in time to the current pump cycle, based on the known difference ("pump frequency difference") between the current pump frequency and the pump frequency associated with the retrieved reference profile. The amplitude scale may also be adjusted to compensate for amplitude changes due to pump frequency, e.g. based on a known function of amplitude as a function of pump frequency. FIG. 13 illustrates a reference profile $r_1(n)$ obtained at a flow rate of 470 ml/min, and a predicted signal profile u(n) which is obtained by scaling the reference profile to a flow rate of 480 ml/min. For comparison only, a reference profile $r_{actual}(n)$ obtained at 480 ml/min is also shown, to illustrate that extrapolation process indeed may yield a properly predicted signal profile.

In a second example, the reference profiles stored in the reference library are temporal profiles. The reference library is again searched based on current pump frequency. If no exact match is found to the current pump frequency, a combination process is executed to generate the predicted signal profile. Here, the reference profiles associated with the two closest matching pump frequencies are retrieved and combined. The combination may be done by re-scaling the pump cycle time of the retrieved reference profiles to the current pump frequency and by calculating the predicted signal profile via interpolation of the re-scaled reference profiles. For example, the predicted signal profile u(n) at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved reference profiles, obtained at a pump frequency $v_i$ and $v_j$, respectively, after re-scaling to the current pump frequency v, and g is a relaxation parameter which is given as a function of the frequency difference $(v-v_i)$, wherein $v_i \le v \le v_j$ and $0 \le g \le 1$. The skilled person realizes that the predicted signal profile u(n) may be generated by combining more than two reference profiles.

Figure 14A:
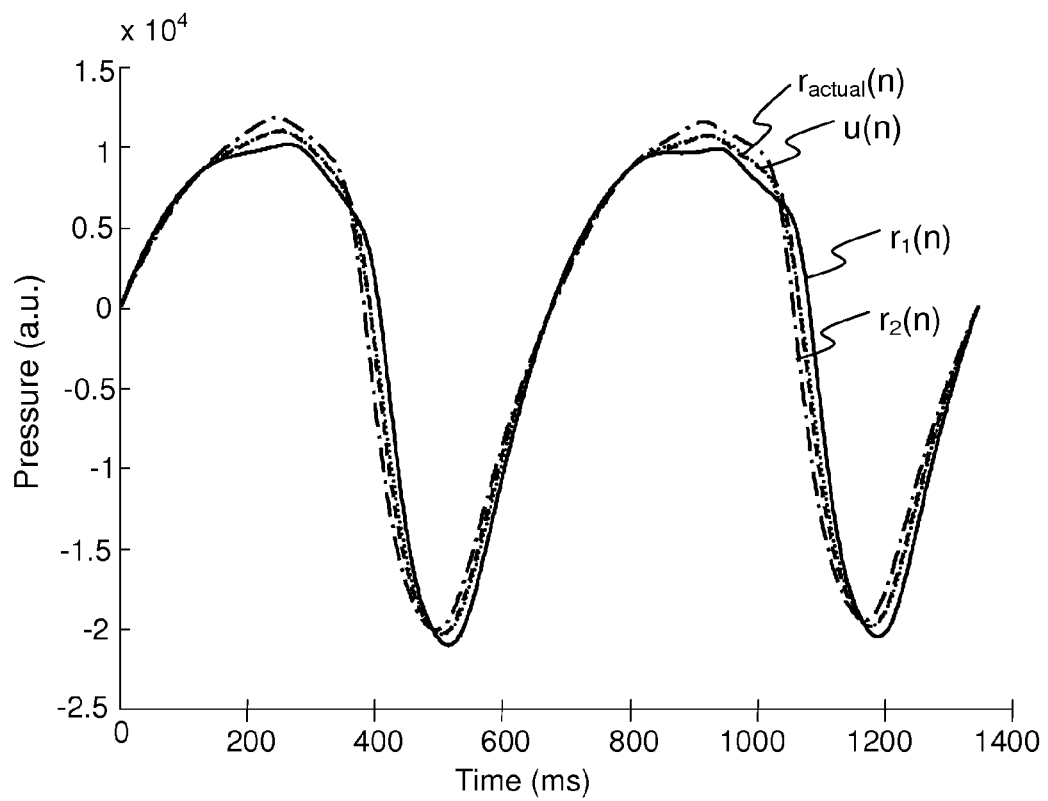
FIG. 14($a$) is a plot to illustrate an interpolation process for generating a predicted signal profile, and FIG. 14($b$) is an enlarged view of FIG. 14($a$).
Figure 14B:
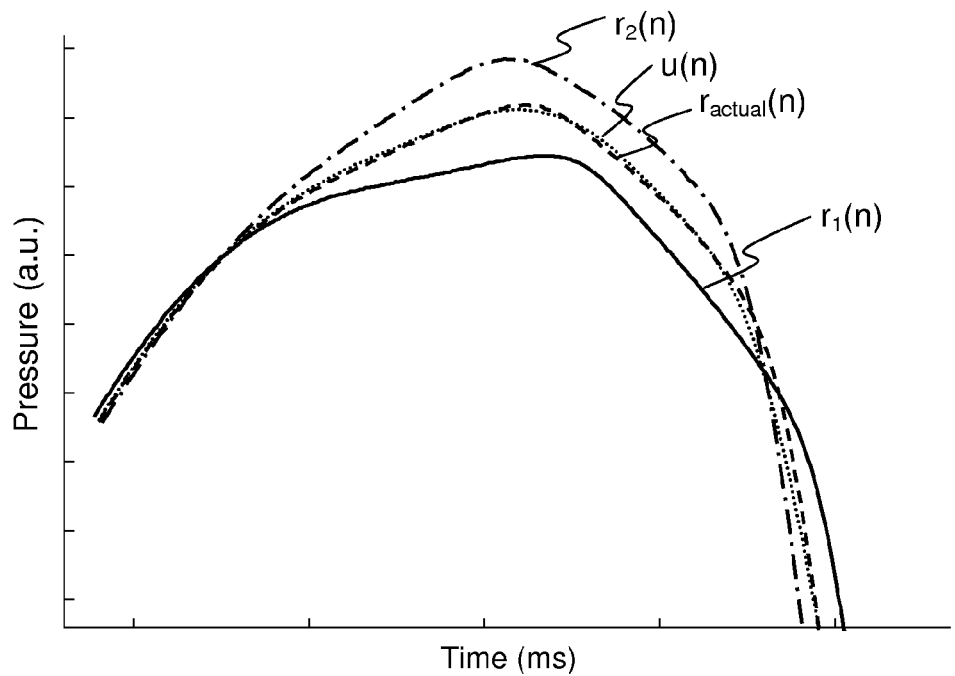

FIG. 14(a) illustrates a predicted signal profile u(n) at a current flow rate of 320 ml/min for a pressure signal obtained from the venous sensor 4c in the system of FIG. 1. The predicted signal profile u(n) has been calculated as an average of a reference profile $r_1(n)$ obtained at a flow rate of 300 ml/min from the venous sensor and a reference profile $r_2(n)$ obtained at a flow rate of 340 ml/min from the venous sensor. For comparison only, a reference profile $r_{actual}(n)$ obtained at 320 ml/min is also shown, to illustrate that the combination process indeed may yield a properly predicted signal profile. In fact, the differences are so small that they are only barely visible in the enlarged view of FIG. 14(b).

The first and second examples may be combined, e.g. by executing the extrapolation process of the first example if the pump frequency difference is less than a certain limit, and otherwise executing the combination process of the second example.

In a third embodiment, like in the second embodiment shown in FIG. 12, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data are then stored in a reference library together with the associated system parameter values (cf. step 1201 in FIG. 12). The implementation of the reference library may be the same as in the second embodiment.

During the actual monitoring process, i.e. when pump pulses are to be eliminated from the pressure signal, a current value of one or more system parameters is obtained from the extracorporeal circuit (cf. step 1202 in FIG. 12). The current value is then matched against the system parameter values in the reference library. Based on the matching, a specific set of energy and phase data may be retrieved from the reference library to be used for generating the predicted signal profile (cf. step 1203 in FIG. 12). The predicted signal profile may be temporal and may be generated by adding sinusoids of appropriate frequency, amplitude and phase, according to the retrieved energy and phase data (cf. step 1204 in FIG. 12).

Generally speaking, without limiting the present disclosure, it may be advantageous to generate the predicted signal profile from energy and phase data when the pump pulses (to be removed) contain only one or a few base frequencies (and harmonics thereof), since the predicted signal profile may be represented by a small data set (containing energy and phase data for the base frequencies and the harmonics). On the other hand, when the power spectrum of the pump pulses is more complex, e.g. a mixture of many base frequencies, it may instead be preferable to generate the predicted signal profile from one or more temporal reference profiles.

Figure 15A:
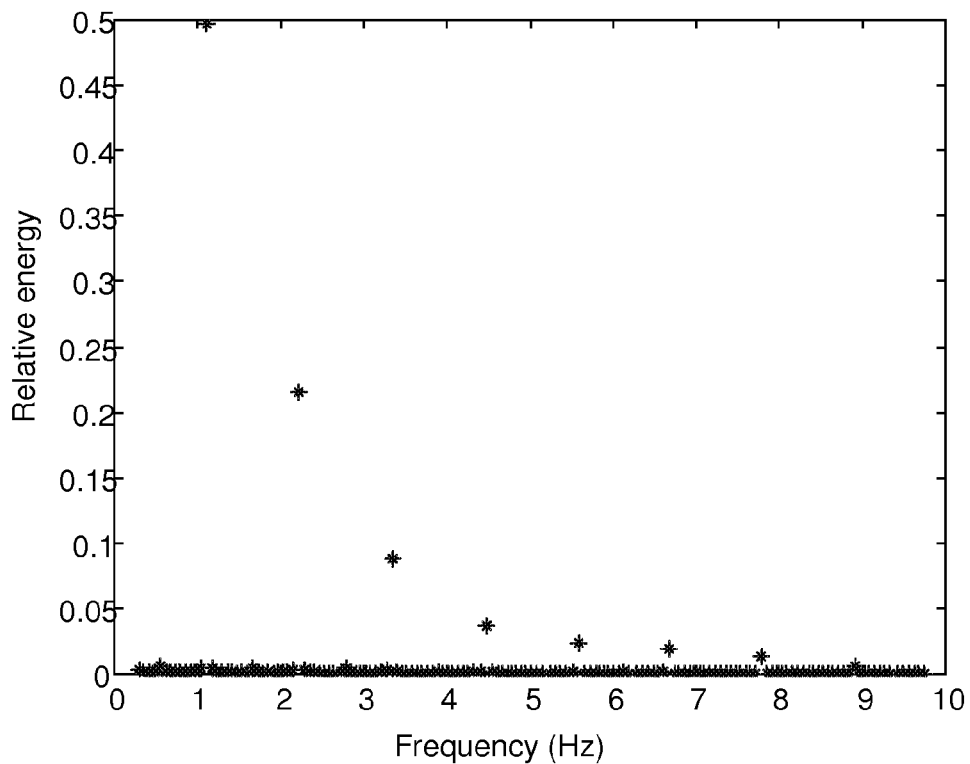
FIG. 15($a$) represents a frequency spectrum of pump pulses at one flow rate, FIG. 15($b$) represents corresponding frequency spectra for three different flow rates, wherein each frequency spectrum is given in logarithmic scale and mapped to harmonic numbers, FIG. 15($c$) is a plot of the data in FIG. 15($b$) in linear scale, and FIG. 15($d$) is a phase angle spectrum corresponding to the frequency spectrum in FIG. 15($a$).
Figure 15B:
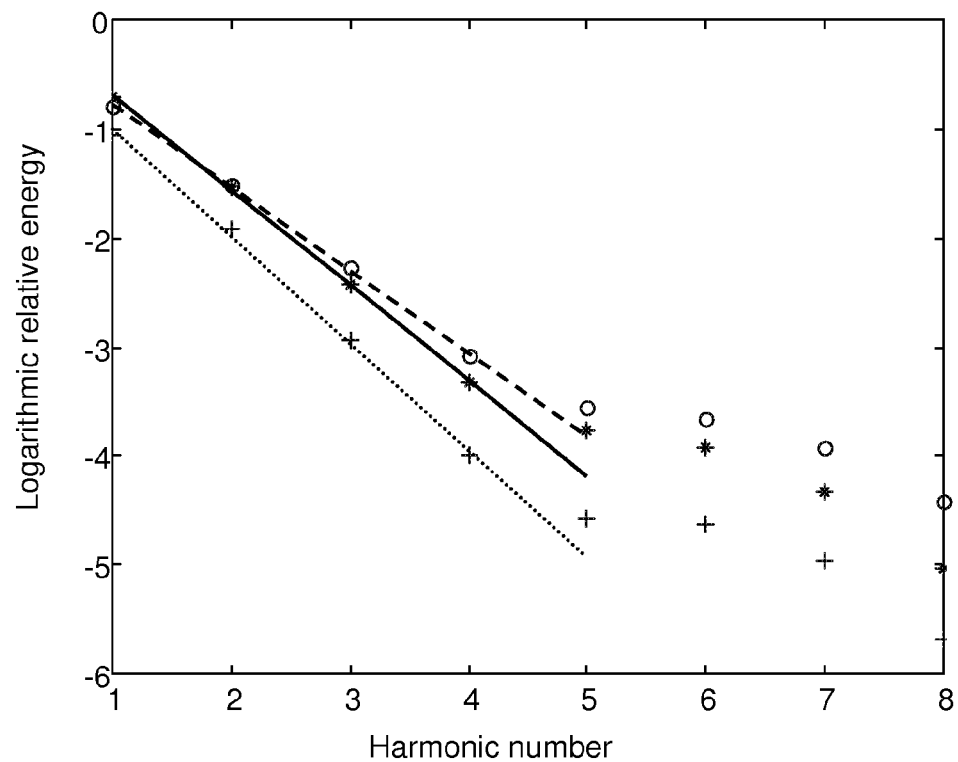
Figure 15C:
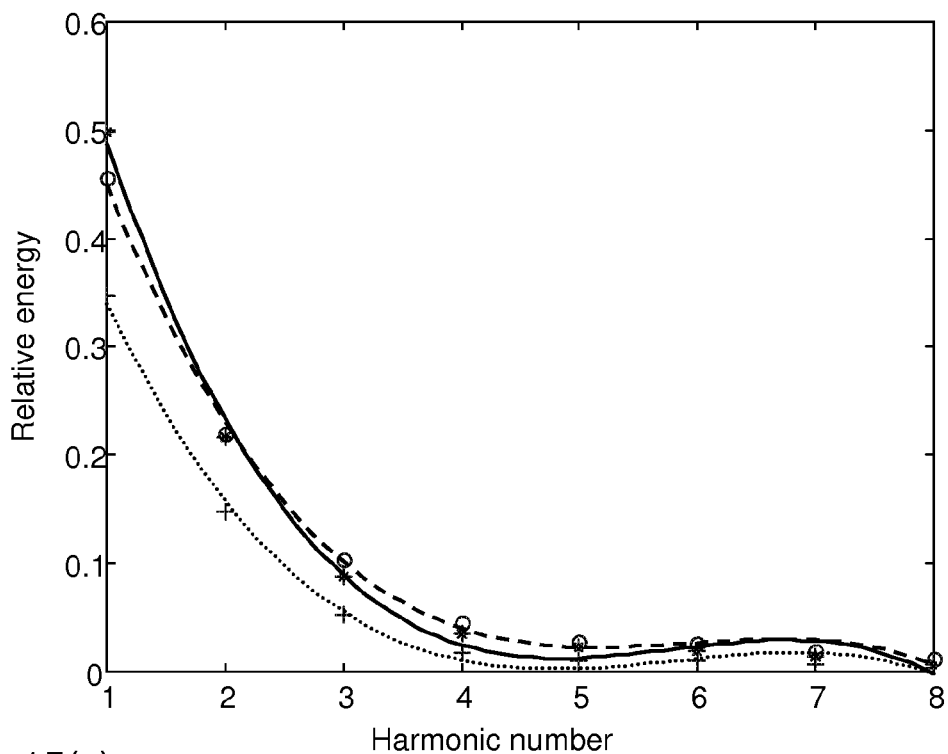

FIG. 15(a) represents an energy spectrum of a reference signal acquired at a flow rate of 300 ml/min in the system of FIG. 1. In this example, the reference signal essentially consists of a basic pump frequency at 1.2 Hz ($f_0$, first harmonic) and a set of overtones of this frequency (second and further harmonics). Compared to the power spectrum of FIG. 9(b), the pressure signals used for generating the graphs in FIG. 15(a)-15(d) do not contain any significant frequency component at $0.5f_0$ and its harmonics. The graph in FIG. 15(a) displays the relative energy distribution, wherein the energy values have been normalized to the total energy for frequencies in the range of 0-10 Hz. FIG. 15(b) represents energy spectra of reference signals acquired at three different flow rates in the system of FIG. 1. The energy spectra are given in logarithmic scale versus harmonic number (first, second, etc). As shown, an approximate linear relationship may be identified between the logarithmic energy and harmonic number for the first four to five harmonic numbers. This indicates that each energy spectrum may be represented by a respective exponential/polynomial function. FIG. 15(c) illustrates the data of FIG. 15(b) in linear scale, wherein a respective polynomial function has been fitted to the data. As indicated in FIGS. 15(a)-15(c), the energy spectra may be represented in different formats in the reference library, e.g. as a set of energy values associated with discrete frequency values or harmonic numbers, or as an energy function representing energy versus frequency/harmonic number.

Figure 15D:
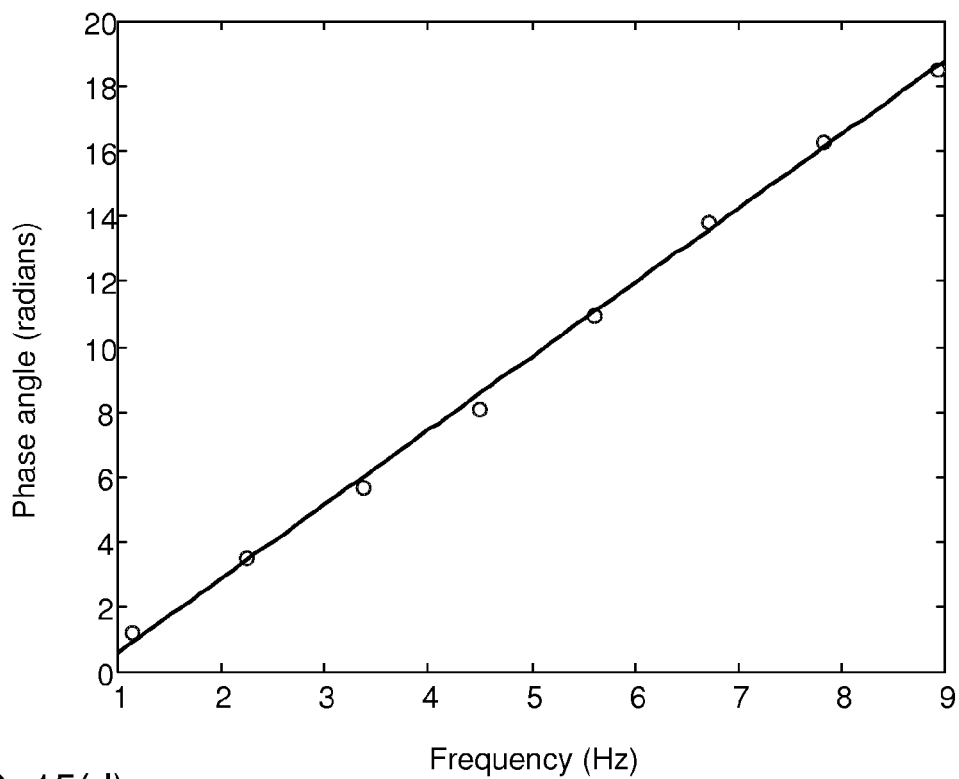

FIG. 15(d) illustrates a phase angle spectrum acquired together with the energy spectrum in FIG. 15(a), i.e. for a flow rate of 300 ml/min. The graph in FIG. 15(d) illustrates phase angle as a function of frequency, and a linear function has been fitted to the data. In an alternative representation (not shown), the phase spectrum may be given as a function of harmonic number. Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library may be used to generate the predicted signal profile. Each energy value in the energy data corresponds to an amplitude of a sinusoid with a given frequency (the frequency associated with the energy value), wherein the phase value for the given frequency indicates the proper phase angle of the sinusoid. This method of preparing the predicted signal profile by combining (typically adding) sinusoids of appropriate frequency, amplitude and phase angle allows the predicted signal profile to include all harmonics of the pump frequency within a desired frequency range.

When a predicted signal profile is to be generated, the reference library is first searched based on a current value of one or more system parameters, such as the current pump frequency. If no exact match is found in the reference library, a combination process may be executed to generate the predicted signal profile. For example, the two closest matching pump frequencies may be identified in the reference library and the associated energy and phase data may be retrieved and combined to form the predicted signal profile. The combination may be done by interpolating the energy data and the phase data. In the example of FIGS. 15(a)-15(d), an interpolated energy value may be calculated for each harmonic number, and similarly an interpolated phase value may be calculated for each harmonic number. Any type of interpolation function may be used, be it linear or non-linear.

In the first, second and third embodiments, one and the same pressure sensor is suitably used in both the reference measurement and the actual monitoring process. Alternatively, different pressure sensor units may be used, provided that the pressure sensor units yield identical signal responses with respect to the pump pulses or that the signal responses may be matched using a known mathematical relationship.

To further improve the first, second and third embodiments, the process of generating the predicted signal profile may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or look-up tables.

In further variations, the second and third embodiments may be combined, e.g. in that the reference library stores not only energy and phase data, but also reference profiles, in association with system parameter value(s). When an exact match is found in the library, the reference profile is retrieved from the library and used as the predicted signal profile, otherwise the predicted signal profile is obtained by retrieving and combining (e.g. interpolating) the energy and phase data, as in the third embodiment. In a variant, the predicted signal profile u(n) at the current pump frequency v is obtained by:

$$u(n)=r_i(n)-r^f_i(n)+r^f(n),$$

wherein $r_i(n)$ denotes a reference profile that is associated with the closest matching pump frequency $v_i$ in the reference library, $r^f_i(n)$ denotes a reference profile that is reconstructed from the energy and phase data associated with the closest matching pump frequency $v_i$ in the reference library, and $r^f(n)$ denotes an estimated reference profile at the current pump frequency v. The estimated reference profile $r^f(n)$ may be obtained by applying predetermined functions to estimate the energy and phase data, respectively, at the current pump frequency v based on the energy and phase data associated with the closest matching pump frequency $v_i$. With reference to FIGS. 15(b)-15(c), such a predetermined function may thus represent the change in energy data between different flow rates. Alternatively, the estimated reference profile $r^f(n)$ may be obtained by retrieving and combining (e.g. interpolating) energy and phase data for the two closest matching pump frequencies $v_i$ and $v_j$ as in the third embodiment.

In a further variant, the reference measurement is made during regular operation of the extracorporeal circuit 20, instead of or in addition to any reference measurements made before regular operation (e.g. during priming or simulated treatments with blood). This reference measurement may be made obtaining the reference signal from a pressure sensor which is substantially isolated from the pressure waves originating from the patient, and use the reference signal for generating the predicted signal profile (optionally after adjustment/modification for differences in confounding factors), which is then used for removing pump pulses from the pressure signal. For example, the reference signal may be obtained from the system sensor 4b (FIG. 1) which may be essentially isolated from the pressure waves originating from the patient.

Simulations

As an alternative to the use of reference measurements, the predicted signal profile may be obtained directly through simulations, i.e. calculations using a mathematical model of the extracorporeal circuit 20, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model may be anything from a complete physical description of the system to a simple function. In one example, such a simple function may convert data on the instantaneous angular velocity of the pump rotor 3' to a predicted signal profile, using empirical or theoretical data. Such data on the instantaneous angular velocity might be obtained from the pump sensor 25 in FIG. 1.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

VII. Time Domain Filtering

There are several different ways of removing one or more pump pulses from the pressure signal, using a predicted signal profile of the pump pulses (e.g. obtained as described in Section VI above). Here, two different removal processes will be described: Single Subtraction and Adaptive Filtering. Of course, the description of removal processes and their implementations is not comprehensive (neither of the different alternatives, nor of the implementations), which is obvious to a person skilled in the art.

Depending on implementation, the predicted signal profile may be input to the removal process as is, or the predicted signal profile may be duplicated to construct an input signal of suitable length for the removal process.

Single Subtraction

In this removal process, a single predicted signal profile is subtracted from the pressure signal. The predicted signal profile may be shifted and scaled in time and scaled in amplitude in any way, e.g. to minimize the error of the removal. Different minimization criterions may be used for such an auto-scaling, e.g., minimizing the sum of the squared errors, or the sum of the absolute errors. Alternatively or additionally, the predicted signal profile is shifted in time based on timing information that indicates the expected timing of the pump pulse(s) in the pressure signal. The timing information may be obtained in the same way as described above (cf. Section VI) in relation to the averaging of pressure segments in the reference signal.

One potential limitation of this removal process is that the relationship between different frequencies in the predicted signal profile is always the same, since the process only shifts and scales the predicted signal profile. Thus, it is not possible to change the relationship between different harmonic frequencies, neither is it possible to use only some of the frequency content in the predicted signal profile and to suppress other frequencies. To overcome this limitation, adaptive filtering may be used since it uses a linear filter before subtraction, e.g. as described in the following.

Adaptive Filtering

Figure 16:
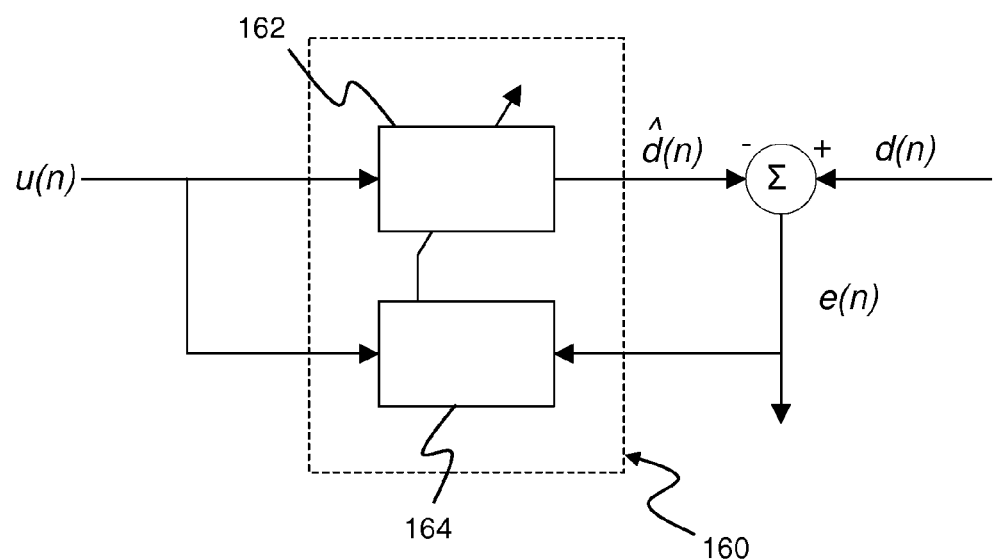
FIG. 16 is schematic view of an adaptive filter structure operable to filter a pressure signal based on a predicted signal profile.

FIG. 16 is a schematic overview of an adaptive filter 160 and an adaptive filter structure which is designed to receive the predicted signal profile u(n) and a pressure signal d(n), and to output an error signal e(n) which forms the aforesaid monitoring signal in which the pump pulses are removed.

Adaptive filters are well-known electronic filters (digital or analog) that self-adjust their transfer function according to an optimizing algorithm. Specifically, the adaptive filter 160 includes a variable filter 162, typically a finite impulse response (FIR) filter of length M with filter coefficients w(n).

Even if adaptive filters are known in the art, they are not readily applicable to cancel the pump pulses in the pressure signal d(n). In the illustrated embodiment, this has been achieved by inputting the predicted signal profile u(n) to the variable filter 162, which processes the predicted signal profile u(n) to generate an estimation signal $\hat{d}(n)$, and to an adaptive update algorithm 164, which calculates the filter coefficients of the variable filter 162 based on the predicted signal profile u(n) and the error signal e(n). The error signal e(n) is given by the difference between the pressure signal d(n) and the estimation signal $\hat{d}(n)$.

Basically, the calculation of the error signal e(n) involves a subtraction of the predicted signal profile u(n) from the pressure signal d(n), since each of the filter coefficients operates to shift and possibly re-scale the amplitude of the predicted signal profile u(n). The estimation signal $\hat{d}(n)$, which is subtracted from the pressure signal d(n) to generate the error signal e(n), is thus formed as a linear combination of M shifted and amplitude-scaled predicted signal profiles u(n).

The adaptive update algorithm 164 may be implemented in many different ways, some of which will be described below. The disclosure is in no way limited to these examples, and the skilled person should have no difficulty of finding further alternatives based on the following description.

There are two main approaches to adaptive filtering: stochastic and deterministic. The difference lies in the minimization of the error signal e(n) by the update algorithm 164, where different minimization criteria are obtained whether e(n) is assumed to be stochastic or deterministic. A stochastic approach typically uses a cost function J with an expectation in the minimization criterion, while a deterministic approach typically uses a mean. The squared error signal $e^2(n)$ is typically used in a cost function when minimizing e(n), since this results in one global minimum. In some situations, the absolute error |e(n)| may be used in the minimization, as well as different forms of constrained minimizations. Of course, any form of the error signal may be used, however convergence towards a global minimum is not always guaranteed and the minimization may not always be solvable.

In a stochastic description of the signal, the cost function may typically be according to, $$J(n)=E\{|e(n)|^2\},$$

and in a deterministic description of the signal the cost function may typically be according to, $$J(n)=\Sigma e^2(n).$$

The pump pulses will be removed in the estimation signal $\hat{d}(n)$ when the error signal e(n) (cost function J(n)) is minimized. Thus, the error signal e(n) will be cleaned from pump pulses while retaining the patient pulses, once the adaptive filter 160 has converged and reached the minimum error.

In order to obtain the optimal filter coefficients w(n) for the variable filter 162, the cost function J needs to be minimized with respect to the filter coefficients w(n). This may be achieved with the cost function gradient vector $\nabla J$, which is the derivative of J with respect to the different filter coefficients $w_0, w_1, \ldots, w_{M-1}$. Steepest Descent is a recursive method (not an adaptive filter) for obtaining the optimal filter coefficients that minimize the cost function J. The recursive method is started by giving the filter coefficients an initial value, which is often set to zero, i.e., w(0)=0. The filter coefficients is then updated according to, $$w(n+1) = w(n) + \frac{1}{2}\mu[-\nabla J(n)],$$

where w is given by, $$w=[w_0\, w_1 \ldots w_{M-1}]^T M\times 1$$

Furthermore, the gradient vector $\nabla J$ points in the direction in which the cost is growing the fastest. Thus, the filter coefficients are corrected in the direction opposite to the gradient, where the length of the correction is influenced through the step size parameter μ. There is always a risk for the Steepest Descent algorithm to diverge, since the algorithm contains a feedback. This sets boundaries on the step size parameter μ in order to ensure convergence. It may be shown that the stability criterion for the Steepest Descent algorithm is given by, $$0 < \mu < \frac{2}{\lambda_{max}}$$

where $\lambda_{max}$ is the largest eigenvalue of R, the correlation matrix of the predicted reference profile u(n), given by $$R = E[\bar{u}(n)\bar{u}^T(n)] = \begin{bmatrix} r(0) & r(1) & \ldots & r(M-1) \\ r(1) & r(0) & & r(M-2) \\ \vdots & \vdots & \ddots & \vdots \\ r(M-1) & r(M-2) & \ldots & r(0) \end{bmatrix},$$

where $\bar{u}(n)$ is given by, $$\bar{u}(n)=[u(n)u(n-1)\ldots u(n-M+1)]^T M\times 1.$$

If the mean squared error (MSE) cost function (defined by $J=E\{|e(n)|^2\}$) is used, it may be shown that the filter coefficients are updated according to, $$w(n+1)=w(n)+\mu E[\bar{u}(n)e(n)],$$

where e(n) is given by, $$e(n)=d(n)-\bar{u}^T(n)w(n).$$

The Steepest Descent algorithm is a recursive algorithm for calculation of the optimal filter coefficients when the statistics of the signals are known. However, this information is often unknown. The Least Mean Squares (LMS) algorithm is a method that is based on the same principles as the Steepest Descent algorithm, but where the statistics is estimated continuously. Thus, the LMS algorithm is an adaptive filter, since the algorithm is able to adapt to changes in the signal statistics (due to continuous statistic estimations), although the gradient may become noisy. Because of the noise in the gradient, the LMS algorithm is unlikely to reach the minimum error $J_{min}$, which the Steepest Descent algorithm does. Instantaneous estimates of the expectation are used in the LMS algorithm, i.e., the expectation is removed. Thus, for the LMS algorithm, the update equation of the filter coefficients becomes $$w(n+1)=w(n)+\mu\bar{u}(n)e(n).$$

The convergence criterion of the LMS algorithm is the same as for the Steepest Descent algorithm. In the LMS algorithm, the step size is proportional to the predicted signal profile u(n), i.e., the gradient noise is amplified when the predicted signal profile is strong. One solution to this problem is to normalize the update of the filter coefficients with $$\|\bar{u}(n)\|^2 = \bar{u}^T(n)\bar{u}(n).$$

The new update equation of the filter coefficients is called the Normalized LMS, and is given by $$w(n+1) = w(n) + \frac{\tilde{\mu}}{a+\|\bar{u}(n)\|^2}\bar{u}(n)e(n),$$

where $0<\tilde{\mu}<2$, and a is a positive protection constant.

There are many more different alternatives to the LMS algorithm, where the step size is modified. One of them is to use a variable adaptation step, $$w(n+1)=w(n)+\alpha(n)\bar{u}(n)e(n),$$

where $\alpha(n)$ for example may be, $$\alpha(n) = \frac{1}{n+c},$$

where c is a positive constant. It is also possible to choose independent adaptation steps for each filter coefficient in the LMS algorithm, e.g., according to, $$w(n+1)=w(n)+A\bar{u}(n)e(n),$$

where A is given by, $$A = \begin{bmatrix} \alpha_1 & 0 & 0 & \cdots & 0 \\ 0 & \alpha_2 & 0 & \cdots & 0 \\ 0 & 0 & \alpha_3 & \cdots & 0 \\ \vdots & \vdots & \vdots & \ddots & \vdots \\ 0 & 0 & 0 & \cdots & \alpha_M \end{bmatrix}.$$

If instead the following cost function $$J(n)=E\{|e(n)|\}$$

is used, then the update equation becomes $$w(n+1)=w(n)+\alpha\text{sign}[e(n)]\bar{u}(n).$$

This adaptive filter is called the Sign LMS, which is used in applications with extremely high requirements on low computational complexity.

Another adaptive filter is the Leaky LMS, which uses a constrained minimization with the following cost function $$J(n)=E\{|e(n)|^2\}+\alpha\|w(n)\|^2.$$

This constraint has the same effect as if white noise with variance a was added to the predicted signal profile u(n). As a result, the uncertainty in the predicted signal profile u(n) is increased, which tends to hold the filter coefficients back. The Leaky LMS is preferably used when R, the correlation matrix of u(n), has one or more eigenvalues equal to zero. However, in systems without noise, the Leaky LMS makes performance poorer. The update equation of the filter coefficients for the Leaky LMS is given by, $$w(n+1)=(1-\mu\alpha)w(n)+\mu\bar{u}(n)e(n).$$

Instead of minimizing the MSE cost function as above, the Recursive Least Squares (RLS) adaptive filter algorithm minimizes the following cost function $$J(n) = \sum_{i=1}^{n} \lambda^{n-i}|e(i)|^2,$$

where $\lambda$ is called forgetting factor, $0<\lambda\leq 1$, and the method is called Exponentially Weighted Least Squares. It may be shown that the update equations of the filter coefficients for the RLS algorithm are, after the following initialization $$w(0)=0_{M\times 1}$$

$$P(0)=\delta^{-1}I_{M\times M}$$

where $I_{M\times M}$ is the identity matrix M×M, given according to $$k(n) = \frac{\lambda^{-1}P(n-1)\bar{u}(n)}{1+\lambda^{-1}\bar{u}^T(n)P(n-1)\bar{u}(n)}$$

$$\xi(n) = d(n) - w^T(n-1)\bar{u}(n)$$

$$w(n) = w(n-1) + k(n)\xi(n)$$

$$P(n) = \lambda^{-1}P(n-1) - \lambda^{-1}k(n)\bar{u}^T(n)P(n-1),$$

where $\delta$ is a small positive constant for high signal-to-noise ratio (SNR), and a large positive constant for low SNR, $\delta<<0.01\sigma_u^2$, and $\xi(n)$ corresponds to e(n) in the preceding algorithms. During the initialization phase the following cost function $$J(n) = \sum_{i=1}^{n} \lambda^{n-i}|e(i)|^2 + \delta\lambda^n\|w(n)\|^2,$$

is minimized instead, due to the use of the initialization $P(0)=\delta^{-1}I$. The RLS algorithm converges in approximately 2M iterations, which is considerably faster than for the LMS algorithm. Another advantage is that the convergence of the RLS algorithm is independent of the eigenvalues of R, which is not the case for the LMS algorithm.

Several RLS algorithms running in parallel may be used with different $\lambda$ and $\delta$, which may be combined in order to improve performance, i.e., $\lambda=1$ may also be used in the algorithm (steady state solution) with many different $\delta$:s.

It should be noted that both the LMS algorithm and the RLS algorithm may be implemented in fixed-point arithmetic, such that they may be run on a processor that has no floating point unit, such as a low-cost embedded microprocessor or microcontroller.

Irrespective of implementation, the performance of the adaptive filter 160 may be further improved by switching the adaptive filter 160 to a static mode, in which the update algorithm 164 is disabled and thus the filter coefficients of the filter 162 are locked to a current set of values. The switching of the adaptive filter 160 may be controlled by an external process that analyses the patient pulses in the error signal e(n), typically in relation to pump pulse data. The pump pulse data may be obtained from the pressure signal, a reference signal (see above), a dedicated pump sensor, a control unit for the blood pump, etc. The adaptive filter 160 may be switched into the static mode if the external process reveals that the rate of patient pulses starts to approach the rate of the pump pulses and/or that the amplitude of the patient pulses is very weak (in relation to an absolute limit, or in relation to a limit given by the amplitude of the pump pulses). The adaptive filter 160 may remain in static mode for a predetermined time period, or until released by the external process.

In a variant, a predicted signal profile of the patient pulses (denoted "predicted physiological profile") is used as input signal to the adaptive filter 160 (instead of the predicted signal profile of the pump pulses), and the monitoring signal is formed by the estimation signal $\hat{d}(n)$ (instead of the error signal e(n)). The foregoing discussion with respect to adaptive filters is equally applicable to this variant.

The invention has mainly been described above with reference to a few embodiments. However, as is readily appreciated by a person skilled in the art, other embodiments than the ones disclosed above are equally possible within the scope and spirit of the invention, which is defined and limited only by the appended claims.

For example, some of the filtering techniques described above in relation to step 1003' and/or step 1003" may automatically be achieved by down-sampling of the pressure/measurement signal, since the desired filtering may be achieved by the anti-aliasing filter included in a down-sampling signal processing algorithm. Additionally, some of the above-described filtering techniques may also be achieved directly in hardware, e.g., in the Analogue-to-Digital (A/D) conversion by choosing an appropriate sample frequency, i.e. due to the anti-aliasing filter which is applied before sampling.

Although the main controller 23 has been described as a single physical unit, it may alternatively be made up of several physical units. For example, the different embodiments for system control as described herein may be implemented by a dedicated control unit, which operates independently from or in cooperation with other control units that are configured to control respective a set of functions of the apparatus for blood treatment, or a component thereof.

Further, in certain embodiments, the connection system C may be configured without dedicated connectors for coupling to connectors in the extracorporeal circuit 20. For example, the access devices 1, 14 may be directly attached to the arterial and venous tube segments 2b, 12a. In such a variant, the connection system C is formed by the access devices 1, 14 and the joints between the access devices 1, 14 and the tube segments 2b, 12a. In such a variant, the fluid connection between the patient and the extracorporeal circuit 20 is formed by connecting at least one access device 1, 14 to the blood vessel access of the patient.

Embodiments of the invention are also applicable when the connection system comprises a single access device, such as in so-called single needle treatment.

Further, embodiments of the invention are applicable for system control in all types of extracorporeal blood flow circuits in which blood is taken from a patient's circulation to have a process applied to it before it is returned to the circulation. Such blood flow circuits include, but are not limited to, hemodialysis, hemofiltration, hemodiafiltration, plasmapheresis, apheresis, extracorporeal membrane oxygenation, assisted blood circulation, extracorporeal liver support/dialysis, and blood fraction separation (e.g. cells) of donor blood, etc.

All of the above-described embodiments, variants, examples, aspects and implementations are equally applicable to system control outside the field of blood treatment. One such alternative field includes extracorporeal circuits operable to collect blood, or components of the blood, from a human or animal subject, e.g. for the purpose of blood donation. Another alternative field includes fluid circuits operable to infuse any type of liquid into a human or animal subject. Such a liquid may e.g. contain blood, medication, vitamins, vaccines, hormones, nutrition, insulin, water, or combinations thereof. All of these types of fluid circuits typically contain a fluid pathway for conducting the liquid to or from the subject, and a pumping device to impart a desired motion to the liquid in the fluid pathway. Further, these fluid circuits may be included in an apparatus which is operable to switch between a fluid transfer mode (analogous with the blood treatment mode), in which the fluid circuit is operated to transfer the liquid to or from the vascular system of the subject via a connection system and the fluid pathway, and a preparatory mode (analogous with the pre-treatment mode), which is executed in preparation for the fluid transfer mode. In fluid circuits without circulation of fluid, i.e. where a fluid is only withdrawn from or infused into the vascular system, the preparatory mode is typically a pre-transfer mode without transfer of liquid between the fluid circuit and the vascular system.

The above-described control method may executed by a control device (cf. 23 in FIG. 1), which may be implemented by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The control device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software, and the adjustment factors, may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The control device may include one or more communication interfaces, such as a serial interface, a parallel interface, a USB interface, a wireless interface, a network adapter, etc, as well as one or more data acquisition devices, such as an A/D converter. The special-purpose software may be provided to the control device on any suitable computer-readable medium, including a record medium, a read-only memory, or an electrical carrier signal.

It is also conceivable that some (or all) method steps are fully or partially implemented by dedicated hardware, such as an FPGA, an ASIC, or an assembly of discrete electronic components (resistors, capacitors, operational amplifier, transistors, filters, etc), as is well-known in the art.

In the following, a set of items are recited to summarize some aspects and embodiments of the invention as disclosed in the foregoing.

Item 1. A control system in an apparatus (200) for extracorporeal blood treatment, wherein said apparatus comprises an extracorporeal blood circuit (20) and a connection system (C) for connecting the extracorporeal blood circuit (20) to the vascular system of a patient, wherein the extracorporeal blood circuit (20) comprises a blood processing device (6), and at least one pumping device (3), said control system being operable to switch between a pre-treatment mode and a blood treatment mode, wherein the blood treatment mode involves operating said at least one pumping device (3) to pump blood from the vascular system via the connection system (C) through the blood processing device (6) and back to the vascular system via the connection system (C), said control system comprising:

an input (28) for obtaining measurement data from at least one energy transfer sensor (40) arranged to sense a transfer of energy between the patient and the connection system (C) or between the patient and the extracorporeal blood circuit (20); and a signal processor (29) connected to the input (28) and being configured to, in the pre-treatment mode, process the measurement data for identification of a characteristic change indicating a connection of the extracorporeal blood circuit (20) to the vascular system of the patient, and, upon such identification, take a dedicated action.

Item 2. The control system of item 1, wherein the transfer of energy involves at least one of a pressure wave and an electrical current.

Item 3. The control system of item 1 or 2, wherein the dedicated action comprises activating at least part of a patient protection system, which is configured to identify fault conditions in at least one of the extracorporeal blood circuit (20), the connection system (C) and the patient.

Item 4. The control system of item 3, wherein the patient protection system comprises at least one of a sub-system for detecting air in the extracorporeal blood circuit (20), a sub-system for detecting blood leakage from the extracorporeal blood circuit (20), a sub-system for detecting a disconnection of the connection system (C), a sub-system for detecting hypotension, and a sub-system for ensuring proper DC pressure level in the extracorporeal blood circuit (20).

Item 5. The control system of any one of items 1-4, wherein the dedicated action comprises allowing entry into the blood treatment mode.

Item 6. The control system of item 5, wherein the dedicated action further comprises automatically entering the blood treatment mode.

Item 7. The control system of item 5, wherein the dedicated action further comprises enabling manual start of the blood treatment mode.

Item 8. The control system of any preceding item, wherein the dedicated action comprises starting said at least one pumping device (3).

Item 9. The control system of any one of items 1-8, wherein the measurement data comprises first and second measurement signals from first and second energy transfer sensors (4a, 4c) in the extracorporeal blood circuit (20), wherein the first energy transfer sensor (4a) is associated with an arterial-side of the extracorporeal blood circuit (20), and the second energy transfer sensor (4c) is associated with a venous-side of the extracorporeal blood circuit (20), and wherein the signal processor (29) is configured to take a different dedicated action depending on the identification of the characteristic change in the first and/or second measurement signals.

Item 10. The control system of item 9, wherein the signal processor (29) is configured to enable entry into the blood treatment mode only upon identification of the characteristic change in the first measurement signal and in the second measurement signal.

Item 11. The control system of item 9 or 10, wherein the signal processor (29) is configured to activate at least part of a patient protection system upon identification of the characteristic change at least one of the first and second measurement signals.

Item 12. The control system of any one items 9-11, wherein the signal processor (29) is further configured to, upon identification of the characteristic change, operate said at least one pumping device (3) to draw blood from the vascular system via the connection system (C) for a time period until the extracorporeal blood circuit (20) is at least partially filled with blood.

Item 13. The control system of item 12, wherein the time period is ended when a dedicated blood detector in the extracorporeal blood circuit (20) indicates presence of blood.

Item 14. The control system of item 12 or 13, wherein said at least part of the patient protection system involves estimating the amount of blood drawn from the vascular system by dead reckoning based on a parameter of said at least one pumping device (3), and terminating the operation of said at least one pumping device (3) if the estimated amount exceeds a threshold value.

Item 15. The control system of any preceding item, wherein the connection system (C) comprises an arterial access device (1) for connecting the arterial-side of the extracorporeal blood circuit (20) to the vascular system, and a venous access device (14) for connecting the venous-side of the extracorporeal blood circuit (20) to the vascular system.

Item 16. The control system of item 1 or 2, wherein the pre-treatment mode involves operating the extracorporeal blood circuit (20) to generate a flow of priming liquid through the extracorporeal blood circuit (20), and wherein the dedicated action comprises stopping the flow of priming liquid.

Item 17. The control system of any preceding item, wherein the signal processor (29) is configured to identify the characteristic change by identifying a step change in the measurement data.

Item 18. The control system of any preceding item, wherein the signal processor (29) is configured to identify the characteristic change by identifying, in the measurement data, at least one pulse originating from a pulse generator.

Item 19. The control system of any preceding item, wherein said energy originates from an energy source associated with the patient, and wherein said at least one energy transfer sensor (40) is associated with at least one of the extracorporeal blood circuit (20) and the connection system (C).

Item 20. The control system of item 19, wherein the energy source comprises a physiological pulse generator in the patient.

Item 21. The control system of item 19 or 20, wherein said at least one energy transfer sensor (40) is configured to detect a pressure wave generated by the energy source.

Item 22. The control system of item 21, wherein the measurement data comprises at least one first pulse representing the pressure wave and at least one interference pulse, wherein the signal processor (29) is configured to process the measurement data to essentially eliminate said at least one interference pulse.

Item 23. The control system of item 22, wherein the signal processor (29) is configured to obtain a pulse profile (u(n)) which is a predicted temporal signal profile of the interference pulse, and to filter the measurement data in the time domain, using the pulse profile (u(n)), to essentially eliminate the interference pulse while retaining the first pulse.

Item 24. The control system of item 23, wherein the signal processor (29) is configured to subtract the pulse profile (u(n)) from the measurement data.

Item 25. The control system of item 24, wherein the signal processor (29) is configured to, before subtracting the pulse profile (u(n)), adjust at least one of the amplitude, the time scale and the phase of the pulse profile (u(n)) with respect to the measurement data.

Item 26. The control system of item 25, wherein the signal processor (29) is configured to minimize a difference between the pulse profile (u(n)) and the measurement data.

Item 27. The control system of any one of items 24-26, wherein said at least one interference pulse originates from said at least one pumping device (3) in the extracorporeal blood circuit (20), and wherein the signal processor (29) is configured to subtract the pulse profile (u(n)) by adjusting a phase of the pulse profile (u(n)) in relation to the measurement data, wherein said phase is indicated by phase information obtained from at least one of: a pump rate sensor (25) coupled to said at least one pumping device (3), and a controller (24) for said at least one pumping device (3).

Item 28. The control system of item 23, wherein the signal processor (29) comprises an adaptive filter (160) which is arranged to generate an estimation signal ($\hat{d}(n)$), based on the pulse profile (u(n)) and an error signal (e(n)) formed as a difference between the measurement data and the estimation signal ($\hat{d}(n)$), whereby the adaptive filter (160) is arranged to essentially eliminate said at least one interference pulse in the error signal (e(n)). The adaptive filter (160) may be configured to generate the estimation signal ($\hat{d}(n)$) as a linear combination of M shifted pulse profiles (u(n)), and specifically the adaptive filter (160) may be configured to linearly combine M instances of the pulse profile (u(n)), which are properly adjusted in amplitude and phase by the adaptive filter (30).

Item 29. The control system of item 28, wherein the adaptive filter (160) comprises a finite impulse response filter (162) with filter coefficients that operate on the pulse profile (u(n)) to generate the estimation signal ($\hat{d}(n)$), and an adaptive algorithm (164) which optimizes the filter coefficients as a function of the error signal (e(n)) and the pulse profile (u(n)).

Item 30. The control system of item 28 or 29, wherein the signal processor (29) is configured to control the adaptive filter (160) to lock the filter coefficients, based on a comparison of the rate and/or amplitude of the first pulses to a limit value.

Item 31. The control system of any one of items 23-30, wherein said at least one interference pulse originates from said at least one pumping device (3) in the extracorporeal blood circuit (20), and wherein the signal processor (29) is configured to, in a reference measurement, cause said at least one pumping device (3) to generate at least one interference pulse, and obtain the pulse profile (u(n)) from a reference signal generated by a reference sensor (4a-4c).

Item 32. The control system of item 31, wherein said at least one pumping device (3) is operated to generate a sequence of interference pulses during the reference measurement, and wherein the pulse profile (u(n)) is obtained by identifying and combining a set of interference pulses in the reference signal.

Item 33. The control system of item 31 or 32, wherein the signal processor (29) is configured to intermittently effect the reference measurement to update the pulse profile (u(n)) during operation of the extracorporeal blood circuit (20).

Item 34. The control system of any one of items 23-30, wherein said at least one interference pulse originates from said at least one pumping device (3) in the extracorporeal blood circuit (20), and wherein the signal processor (29) is configured to obtain the pulse profile (u(n)) based on a predetermined signal profile.

Item 35. The control system of item 34, wherein the signal processor (29) is configured to modify the predetermined signal profile according to a mathematical model based on a current value of one or more system parameters of the extracorporeal blood circuit (20).

Item 36. The control system of any one of items 23-30, wherein said at least one interference pulse originates from said at least one pumping device (3) in the extracorporeal blood circuit (20), and wherein the signal processor (29) is configured to obtain a current value of one or more system parameters of the extracorporeal blood circuit (20), and to obtain the pulse profile (u(n)) as a function of the current value.

Item 37. The control system of item 36, wherein the signal processor (29) is configured to obtain the pulse profile (u(n)) by identifying, based on the current value, one or more temporal reference profiles ($r_1(n)$, $r_2(n)$) in a reference database; and obtaining the pulse profile (u(n)) based on said one or more temporal reference profiles ($r_1(n)$, $r_2(n)$).

Item 38. The control system of item 37, wherein said one or more system parameters is indicative of a pumping rate of said at least one pumping device (3).

Item 39. The control system of item 37 or 38, wherein each temporal reference profile ($r_1(n)$, $r_2(n)$) in the reference database is obtained by a reference measurement in the extracorporeal blood circuit (20) for a respective value of said one or more system parameters.

Item 40. The control system of item 36, wherein the signal processor (29) is configured to obtain the pulse profile (u(n)) by identifying, based on the current value, one or more combinations of energy and phase angle data in a reference database; and obtaining the pulse profile (u(n)) based on said one or more combinations of energy and phase angle data.

Item 41. The control system of item 40, wherein the signal processor (29) is configured to obtain the pulse profile (u(n)) by combining a set of sinusoids of different frequencies, wherein the amplitude and phase angle of each sinusoid is given by said one or more combinations of energy and phase angle data.

Item 42. The control system of item 36, wherein the signal processor (29) is configured to obtain the pulse profile (u(n)) by inputting the current value into an algorithm which calculates the response of the energy transfer sensor (40) based on a mathematical model of the extracorporeal blood circuit (20).

Item 43. The control system of any one of items 22-42, wherein the signal processor (29) is configured to generate a time-dependent monitoring signal in which said at least one interference pulse is essentially eliminated, to calculate a parameter value based on signal values in the monitoring signal, and to identify the characteristic change based at least partly on the parameter value.

Item 44. The control system of item 43, wherein the parameter value represents a temporal distribution of the signal values.

Item 45. The control system of item 43 or 44, wherein the signal processor (29) is configured to calculate the parameter value as a statistical dispersion measure of the signal values.

Item 46. The control system of item 43 or 44, wherein the signal processor (29) is configured to calculate the parameter value by matching the signal values to a predicted temporal signal profile of said at least one first pulse.

Item 47. The control system of item 46, wherein the parameter value is a correlation value resulting from said matching.

Item 48. The control system of item 21, wherein the connection of the extracorporeal blood circuit (20) to the vascular system of the patient causes the measurement data to comprise at least one first pulse representing the pressure wave and at least one interference pulse originating from said at least one pumping device (3), wherein the signal processor (29) is configured to process the measurement data to generate a time-dependent composite signal which represents at least part of said at least one first pulse and at least part of said at least one interference pulse, to calculate a parameter value based on signal values in the composite signal, and to identify the characteristic change based at least partly on the parameter value.

Item 49. The control system of item 48, wherein the parameter value represents a temporal distribution of the signal values.

Item 50. The control system of item 48 or 49, wherein the signal processor (29) is configured to generate the composite signal to represent a signal envelope in the measurement data.

Item 51. The control system of item 50, wherein the signal processor (29) is configured to generate the composite signal by: identifying peaks in the measurement data, and generating a sequence of signal values representing said peaks.

Item 52. The control system of any one of items 48-51, wherein the signal processor (29) is configured to calculate the parameter value as a statistical dispersion measure of the signal values.

Item 53. The control system of any one of items 48-51, wherein the signal processor (29) is configured to generate a frequency domain representation of the signal values, and to calculate the parameter value based on the frequency domain representation.

Item 54. The control system of any one of items 48-51, wherein the signal processor (29) is configured to identify at least one pulse feature in the composite signal, and to calculate the parameter value based on the pulse feature.

Item 55. The control system of item 54, wherein the parameter value is calculated as a symmetry measure between pulse features of a sequence of pulses that are represented in the composite signal.

Item 56. The control system of item 54 or 55, wherein the pulse feature is indicative of at least one of a peak amplitude, a timing and a shape of a pulse that is represented in the composite signal.

Item 57. The control system of any one of items 54-56, wherein the signal processor (29) is configured to calculate the parameter value by comparing at least one pair of pulse features obtained from a set of pulses that are represented in the composite signal.

Item 58. The control system of item 57, wherein the set of pulses is selected to yield a known relation between said at least one pair of pulse features in the absence of a connection between the extracorporeal blood circuit (20) and the vascular system.

Item 59. The control system of any one of items 54-56, wherein the pulse feature is indicative of a shape of a pulse in the composite signal, and wherein the signal processor (29) is configured to calculate the parameter value by comparing the shape to an average signal profile, wherein signal processor (29) is configured to calculate the average signal profile by: deriving, based on timing information indicative of the timing of said at least one interference pulse in the composite signal, a set of signal segments in the composite signal; and aligning and combining the signal segments, based on the timing information, to generate the average signal profile.

Item 60. The control system of any one of items 54-59, wherein the signal processor (29) is configured to identify each pulse feature in the composite signal based on timing information which is indicative of the timing of said at least one interference pulse in the composite signal.

Item 61. The control system of item 54, wherein the pulse feature comprises shape-indicative data, and wherein the signal processor (29) is configured to calculate the parameter value by comparing the shape-indicative data to reference data.

Item 62. The control system of item 61, wherein the reference data is representative of the shape of at least one interference pulse.

Item 63. The control system of item 62, wherein the shape-indicative data comprises signal values in the composite signal, and the reference data comprises a temporal reference profile.

Item 64. The control system of item 63, wherein the signal processor (29) is configured to, in said comparing, obtain timing information indicative of the timing of said at least one interference pulse in the composite signal, and use the timing information to align the signal values in the composite signal with the temporal reference profile.

Item 65. The control system of item 61 or 62, wherein the signal processor (29) is configured to extract the shape-indicative data by an analysis of the frequency content of the composite signal, and wherein the reference data is representative of an amplitude spectrum.

Item 66. The control system of item 65, wherein the signal processor (29) is further configured to extract the shape-indicative data by an analysis of the phase content of the composite signal, and wherein the reference data is further representative of a phase spectrum.

Item 67. The control system of any one of items 61-66, wherein the parameter value is indicative of a similarity or a deviation between the shape-indicative data and the reference data.

Item 68. The control system of any one of items 61-67, wherein the signal processor (29) is further configured to obtain a current value of one or more system parameters of the extracorporeal blood circuit (20), and wherein the signal processor (29) is configured to obtain the reference data as a function of the current value.

Item 69. The control system of item 68, wherein said one or more system parameters is indicative of the rate of interference pulses in the extracorporeal blood circuit (20).

Item 70. The control system of any one of items 1-21, wherein the signal processor is configured to process the measurement data for identification of the characteristic change while the pumping device (3) is inactivated.

Item 71. The control system of any one of items 1-18, wherein said energy originates from an energy source associated with the apparatus (200), and wherein said at least one energy transfer sensor (40) is associated with the patient.

Item 72. The control system of item 71, wherein the energy source comprises the pumping device (3) in the extracorporeal blood circuit (20).

Item 73. A control system in an apparatus (200) for extracorporeal blood treatment, wherein said apparatus comprises an extracorporeal blood circuit (20) and a connection system (C) for connecting the extracorporeal blood circuit (20) to the vascular system of a patient, wherein the extracorporeal blood circuit (20) comprises a blood processing device (6), and at least one pumping device (3), said control system being operable to switch between a pre-treatment mode and a blood treatment mode, wherein the blood treatment mode involves operating said at least one pumping device (3) to pump blood from the vascular system via the connection system (C) through the blood processing device (6) and back to the vascular system via the connection system (C), said control system comprising:

means (28) for obtaining measurement data from at least one energy transfer sensor (40) arranged to sense a transfer of energy between the patient and the connection system (C) or between the patient and the extracorporeal blood circuit (20);

means (29) for processing, when the control system is in the pre-treatment mode, the measurement data for identification of a characteristic change indicating a connection of the extracorporeal blood circuit (20) to the vascular system of the patient; and means (29) for causing a dedicated action upon such identification.

Embodiments of the control system as set forth in item 73 may correspond to the embodiments of the control system as set forth in items 2-72.

Item 100. A method for controlling an apparatus (200) for extracorporeal blood treatment, wherein said apparatus (200) comprises an extracorporeal blood circuit (20) and a connection system (C) for connecting the extracorporeal blood circuit (20) to the vascular system of a patient, wherein the extracorporeal blood circuit (20) comprises a blood processing device (6), and at least one pumping device (3), wherein said apparatus (200) is operable in a pre-treatment mode and a blood treatment mode, wherein the blood treatment mode involves operating said at least one pumping device (3) to pump blood from the vascular system via the connection system (C) through the blood processing device (6) and back to the vascular system via the connection system (C), said method comprising:

obtaining measurement data from at least one energy transfer sensor (40) which is arranged to sense a transfer of energy between the patient and the connection system (C) or between the patient and the extracorporeal blood circuit (20);

while operating the apparatus (200) in the pre-treatment mode, processing the measurement data for identification of a characteristic change indicating a connection of extracorporeal blood circuit (20) to the vascular system of the patient; and upon such identification, causing a dedicated action to be taken.

Item 101. The method of item 100, wherein the transfer of energy involves at least one of a pressure wave and an electrical current.

Item 102. The method of item 100 or 101, wherein the dedicated action comprises activating at least part of a patient protection system, which is configured to identify fault conditions in at least one of the extracorporeal blood circuit (20), the connection system (C) and the patient.

Item 103. The method of item 102, wherein the patient protection system comprises at least one of a sub-system for detecting air in the extracorporeal blood circuit (20), a sub-system for detecting blood leakage from the extracorporeal blood circuit (20), a sub-system for detecting a disconnection of the connection system (C), a sub-system for detecting hypotension, and a sub-system for ensuring proper DC pressure level in the extracorporeal blood circuit (20).

Item 104. The method of any one of items 101-103, wherein the dedicated action comprises allowing entry into the blood treatment mode.

Item 105. The method of item 104, wherein the dedicated action further comprises automatically entering the blood treatment mode.

Item 106. The method of item 104, wherein the dedicated action further comprises enabling manual start of the blood treatment mode.

Item 107. The method of any one of items 100-106, wherein the dedicated action comprises starting said at least one pumping device (3).

Item 108. The method of any one of items 100-107, wherein the measurement data comprises first and second measurement signals from first and second energy transfer sensors (4a, 4c) in the extracorporeal blood circuit (20), wherein the first energy transfer sensor (4a) is associated with an arterial-side of the extracorporeal blood circuit (20), and the second energy transfer sensor (4c) is associated with a venous-side of the extracorporeal blood circuit (20), and said causing the dedicated action comprises: taking a different dedicated action depending on the identification of the characteristic change in the first and/or second measurement signals.

Item 109. The method of item 108, wherein entry into the blood treatment mode is enabled only upon identification of the characteristic change in the first measurement signal and in the second measurement signal.

Item 110. The method of item 108 or 109, wherein at least part of a patient protection system is activated upon identification of the characteristic change at least one of the first and second measurement signals.

Item 111. The method of any one items 108-110, wherein further comprising: operating, upon identification of the characteristic change, said at least one pumping device (3) to draw blood from the vascular system via the connection system (C) for a time period until the extracorporeal blood circuit (20) is at least partially filled with blood.

Item 112. The method of item 111, wherein the time period is ended when a dedicated blood detector in the extracorporeal blood circuit (20) indicates presence of blood.

Item 113. The method of item 12 or 13, wherein said at least part of the patient protection system involves estimating the amount of blood drawn from the vascular system by dead reckoning based on a parameter of said at least one pumping device (3), and terminating the operation of said at least one pumping device (3) if the estimated amount exceeds a threshold value.

Item 114. The method of any one of items 100-113, wherein the connection system (C) comprises an arterial access device (1) for connecting the arterial-side of the extracorporeal blood circuit (20) to the vascular system, and a venous access device (14) for connecting the venous-side of the extracorporeal blood circuit (20) to the vascular system.

Item 115. The method of item 100 or 101, wherein the pre-treatment mode involves operating the extracorporeal blood circuit (20) to generate a flow of priming liquid through the extracorporeal blood circuit (20), and wherein the dedicated action comprises stopping the flow of priming liquid.

Item 116. The method of any one of items 100-115, wherein the characteristic change is identified by identifying a step change in the measurement data.

Item 117. The method of any one of items 100-116, wherein the characteristic change is identified by identifying, in the measurement data, at least one pulse originating from a pulse generator.

Item 118. The method of any one of items 100-117, wherein said energy originates from an energy source associated with the patient, and wherein said at least one energy transfer sensor (40) is associated with at least one of the extracorporeal blood circuit (20) and the connection system (C).

Item 119. The method of item 118, wherein the energy source comprises a physiological pulse generator in the patient.

Item 120. The method of item 118 or 119, wherein said at least one energy transfer sensor (40) is configured to detect a pressure wave generated by the energy source.

Item 121. The method of item 120, wherein the measurement data comprises at least one first pulse representing the pressure wave and at least one interference pulse, wherein the measurement data is processed to essentially eliminate said at least one interference pulse.

Item 122. The method of item 121, wherein further comprising: obtaining a pulse profile (u(n)) which is a predicted temporal signal profile of the interference pulse, and filtering the measurement data in the time domain, using the pulse profile (u(n)), to essentially eliminate the interference pulse while retaining the first pulse.

Item 123. The method of item 122, wherein said filtering comprises: subtracting the pulse profile (u(n)) from the measurement data.

Item 124. The method of item 123, wherein further comprising, before subtracting the pulse profile (u(n)): adjusting at least one of the amplitude, the time scale and the phase of the pulse profile (u(n)) with respect to the measurement data.

Item 125. The method of item 124, wherein further comprising minimizing a difference between the pulse profile (u(n)) and the measurement data.

Item 126. The method of any one of items 123-125, wherein said at least one interference pulse originates from said at least one pumping device (3) in the extracorporeal blood circuit (20), and wherein said subtracting the pulse profile (u(n)) comprises: obtaining phase information from at least one of a pump rate sensor (25) coupled to said at least one pumping device (3), and a controller (24) for said at least one pumping device (3); and adjusting a phase of the pulse profile (u(n)) in relation to the measurement data based on the phase information.

Item 127. The method of item 122, wherein said filtering comprises: operating an adaptive filter (160) to generate an estimation signal ($\hat{d}(n)$), based on the pulse profile (u(n)) and an error signal (e(n)) formed as a difference between the measurement data and the estimation signal ($\hat{d}(n)$), such that the adaptive filter (160) essentially eliminates said at least one interference pulse in the error signal (e(n)). The adaptive filter (160) may be operated to generate the estimation signal ($\hat{d}(n)$) as a linear combination of M shifted pulse profiles (u(n)), and specifically the adaptive filter (160) may be operated to linearly combine M instances of the pulse profile (u(n)), which are properly adjusted in amplitude and phase by the adaptive filter (30).

Item 128. The method of item 127, wherein the adaptive filter (160) comprises a finite impulse response filter (162) with filter coefficients that operate on the pulse profile (u(n)) to generate the estimation signal ($\hat{d}(n)$), and an adaptive algorithm (164) which optimizes the filter coefficients as a function of the error signal (e(n)) and the pulse profile (u(n)).

Item 129. The method of item 127 or 128, further comprising: controlling the adaptive filter (160) to lock the filter coefficients, based on a comparison of the rate and/or amplitude of the first pulses to a limit value.

Item 130. The method of any one of items 122-129, wherein said at least one interference pulse originates from said at least one pumping device (3) in the extracorporeal blood circuit (20), and wherein said method further comprises, in a reference measurement, causing said at least one pumping device (3) to generate at least one interference pulse, and obtaining the pulse profile (u(n)) from a reference signal generated by a reference sensor (4a-4c).

Item 131. The method of item 130, further comprising: operating said at least one pumping device (3) to generate a sequence of interference pulses during the reference measurement, and wherein said obtaining the pulse profile (u(n)) comprises: identifying and combining a set of interference pulses in the reference signal.

Item 132. The method of item 130 or 131, further comprising: intermittently effecting the reference measurement to update the pulse profile (u(n)) during operation of the extracorporeal blood circuit (20).

Item 133. The method of any one of items 122-129, wherein said at least one interference pulse originates from said at least one pumping device (3) in the extracorporeal blood circuit (20), and wherein the pulse profile (u(n)) is obtained based on a predetermined signal profile.

Item 134. The method of item 133, further comprising: modifying the predetermined signal profile according to a mathematical model based on a current value of one or more system parameters of the extracorporeal blood circuit (20).

Item 135. The method of any one of items 122-129, wherein said at least one interference pulse originates from said at least one pumping device (3) in the extracorporeal blood circuit (20), wherein said obtaining the pulse profile (u(n)) comprises: obtaining a current value of one or more system parameters of the extracorporeal blood circuit (20), and obtaining the pulse profile (u(n)) as a function of the current value.

Item 136. The method of item 135, wherein said obtaining the pulse profile (u(n)) comprises: identifying, based on the current value, one or more temporal reference profiles ($r_1(n)$, $r_2(n)$) in a reference database; and obtaining the pulse profile (u(n)) based on said one or more temporal reference profiles ($r_1(n)$, $r_2(n)$).

Item 137. The method of item 136, wherein said one or more system parameters is indicative of a pumping rate of said at least one pumping device (3).

Item 138. The method of item 136 or 137, wherein each temporal reference profile ($r_1(n)$, $r_2(n)$) in the reference database is obtained by a reference measurement in the extracorporeal blood circuit (20) for a respective value of said one or more system parameters.

Item 139. The method of item 135, wherein said obtaining the pulse profile (u(n)) comprises: identifying, based on the current value, one or more combinations of energy and phase angle data in a reference database; and obtaining the pulse profile (u(n)) based on said one or more combinations of energy and phase angle data.

Item 140. The method of item 139, wherein said obtaining the pulse profile (u(n)) comprises: combining a set of sinusoids of different frequencies, wherein the amplitude and phase angle of each sinusoid is given by said one or more combinations of energy and phase angle data.

Item 141. The method of item 135, wherein said obtaining the pulse profile (u(n)) comprises: inputting the current value into an algorithm which calculates the response of the energy transfer sensor (40) based on a mathematical model of the extracorporeal blood circuit (20).

Item 142. The method of any one of items 121-141, wherein said processing the measurement data comprises: generating a time-dependent monitoring signal in which said at least one interference pulse is essentially eliminated, to calculate a parameter value based on signal values in the monitoring signal, and identifying the characteristic change based at least partly on the parameter value.

Item 143. The method of item 142, wherein the parameter value represents a temporal distribution of the signal values.

Item 144. The method of item 142 or 143, wherein further comprising: calculating the parameter value as a statistical dispersion measure of the signal values.

Item 145. The method of item 142 or 143, further comprising: calculating the parameter value by matching the signal values to a predicted temporal signal profile of said at least one first pulse.

Item 146. The method of item 145, wherein the parameter value is a correlation value resulting from said matching.

Item 147. The method of item 120, wherein the connection of the extracorporeal blood circuit (20) to the vascular system of the patient causes the measurement data to comprise at least one first pulse representing the pressure wave and at least one interference pulse originating from said at least one pumping device (3), wherein said processing the measurement data comprises: processing the measurement data to generate a time-dependent composite signal which represents at least part of said at least one first pulse and at least part of said at least one interference pulse, calculating a parameter value based on signal values in the composite signal, and identifying the characteristic change based at least partly on the parameter value.

Item 148. The method of item 147, wherein the parameter value represents a temporal distribution of the signal values.

Item 149. The method of item 147 or 148, wherein the composite signal is generated to represent a signal envelope in the measurement data.

Item 150. The generate of item 149, wherein the composite signal is generated by: identifying peaks in the measurement data, and generating a sequence of signal values representing said peaks.

Item 151. The method of any one of items 147-150, wherein the parameter value is calculated as a statistical dispersion measure of the signal values.

Item 152. The method of any one of items 147-150, further comprising: generating a frequency domain representation of the signal values, and calculating the parameter value based on the frequency domain representation.

Item 153. The method of any one of items 147-150, further comprising: identifying at least one pulse feature in the composite signal, and calculating the parameter value based on the pulse feature.

Item 154. The method of item 153, wherein the parameter value is calculated as a symmetry measure between pulse features of a sequence of pulses that are represented in the composite signal.

Item 155. The method of item 153 or 154, wherein the pulse feature is indicative of at least one of a peak amplitude, a timing and a shape of a pulse that is represented in the composite signal.

Item 156. The method of any one of items 153-155, wherein the parameter value is calculated by comparing at least one pair of pulse features obtained from a set of pulses that are represented in the composite signal.

Item 157. The method of item 156, wherein the set of pulses is selected to yield a known relation between said at least one pair of pulse features in the absence of a connection between the extracorporeal blood circuit (20) and the vascular system.

Item 158. The method of any one of items 153-155, wherein the pulse feature is indicative of a shape of a pulse in the composite signal, and wherein the parameter value is calculated by comparing the shape to an average signal profile, wherein the average signal profile is calculated by: deriving, based on timing information indicative of the timing of said at least one interference pulse in the composite signal, a set of signal segments in the composite signal; and aligning and combining the signal segments, based on the timing information, to generate the average signal profile.

Item 159. The method of any one of items 153-158, wherein each pulse feature in the composite signal is identified based on timing information which is indicative of the timing of said at least one interference pulse in the composite signal.

Item 160. The method of item 153, wherein the pulse feature comprises shape-indicative data, and wherein the parameter value is calculated by comparing the shape-indicative data to reference data.

Item 161. The method of item 160, wherein the reference data is representative of the shape of at least one interference pulse.

Item 162. The method of item 161, wherein the shape-indicative data comprises signal values in the composite signal, and the reference data comprises a temporal reference profile.

Item 163. The method of item 162, wherein said comparing comprises: obtaining timing information indicative of the timing of said at least one interference pulse in the composite signal, and using the timing information to align the signal values in the composite signal with the temporal reference profile.

Item 164. The method of item 160 or 161, further comprising: extracting the shape-indicative data by an analysis of the frequency content of the composite signal, wherein the reference data is representative of an amplitude spectrum Item 165. The method of item 164, further comprising: extracting the shape-indicative data by an analysis of the phase content of the composite signal, wherein the reference data is further representative of a phase spectrum Item 166. The method of any one of items 160-165, wherein the parameter value is indicative of a similarity or a deviation between the shape-indicative data and the reference data.

Item 167. The method of any one of items 160-166, further comprising: obtaining a current value of one or more system parameters of the extracorporeal blood circuit (20), and obtaining the reference data as a function of the current value.

Item 168. The method of item 167, wherein said one or more system parameters is indicative of the rate of interference pulses in the extracorporeal blood circuit (20).

Item 169. The method of any one of items 100-120, wherein the measurement data is processed for identification of the characteristic change while the pumping device (3) is inactivated.

Item 170. The method of any one of items 100-117, wherein said energy originates from an energy source associated with the apparatus (200), and wherein said at least one energy transfer sensor (40) is associated with the patient.

Item 171. The method of item 170, wherein the energy source comprises the pumping device (3) in the extracorporeal blood circuit (20).

Item 200. A computer-readable medium comprising computer instructions which, when executed by a processor, cause the processor to perform the method of any one of items 100-171.

Item 300. A control system in an apparatus (200) for fluid transfer to or from a subject, wherein said apparatus (200) comprises a fluid circuit (20) and a connection system (C) for connecting the fluid circuit (20) to the vascular system of the subject, wherein the fluid circuit (20) comprises a fluid pathway (30) and at least one pumping device (3), said control system being operable to switch between a preparatory mode and a fluid transfer mode, wherein the fluid transfer mode involves operating the fluid circuit (20) to transfer a fluid to or from the vascular system via the connection system (C) and the fluid pathway (30), said control system comprising:

an input (29) for obtaining measurement data from at least one energy transfer sensor (40) arranged to sense a transfer of energy between the subject and the connection system (C) or between the subject and the fluid circuit (20); and a signal processor (29) connected to the input (28) and being configured to, in the preparatory mode, process the measurement data for identification of a characteristic change indicating a connection of the fluid circuit (20) to the vascular system of the subject, and, upon such identification, take dedicated action.

Item 301. A control system in an apparatus (200) for fluid transfer to or from a subject, wherein said apparatus (200) comprises a fluid circuit (20) and a connection system (C) for connecting the fluid circuit (20) to the vascular system of the subject, wherein the fluid circuit (20) comprises a fluid pathway (30) and at least one pumping device (3), said control system being operable to switch between a preparatory mode and a fluid transfer mode, wherein the fluid transfer mode involves operating the fluid circuit (20) to transfer a fluid to or from the vascular system via the connection system (C) and the fluid pathway (30), said control system comprising:

means (28) for obtaining measurement data from at least one energy transfer sensor (40) arranged to sense a transfer of energy between the subject and the connection system (C) or between the subject and the fluid circuit (20);

means (29) for processing, when the control system is in the preparatory mode, the measurement data for identification of a characteristic change indicating a connection of the fluid circuit (20) to the vascular system of the subject; and means (29) for causing a dedicated action upon such identification.

Item 302. A method for controlling an apparatus (200) for fluid transfer to or from a subject, wherein said apparatus (200) comprises a fluid circuit (20) and a connection system (C) for connecting the fluid circuit (20) to the vascular system of a subject, wherein the fluid circuit (20) comprises a fluid pathway (30) and at least one pumping device (3), wherein said apparatus (200) is operable in a preparatory mode and a fluid transfer mode, wherein the fluid transfer mode involves operating the fluid circuit (20) to transfer a fluid to or from the vascular system via the connection system (C) and the fluid pathway (30), said method comprising:

obtaining measurement data from at least one energy transfer sensor (40) which is arranged to sense a transfer of energy between the subject and the connection system (C) or between the subject and the fluid circuit (20);

while operating the apparatus (200) in the preparatory mode, processing the measurement data for identification of a characteristic change indicating a connection of fluid circuit (20) to the vascular system of the subject; and upon such identification, causing a dedicated action to be taken.

In one embodiment of the control systems of items 300-301 and the method of item 302, the fluid circuit is an extracorporeal blood circuit (20) which comprises a blood processing device (6) and said at least one pumping device (3), wherein the fluid transfer mode is a blood treatment mode, wherein the blood treatment mode involves operating said at least one pumping device (3) to pump blood from the vascular system via the connection system (C) through the blood processing device (6) and back to the vascular system via the connection system (C), and wherein the preparatory mode is a pre-treatment mode that precedes the blood treatment mode.

It should be realized that embodiments of the control systems as set forth in items 300 and 301, and the method as set forth in item 302 may correspond to the embodiments as set forth in items 2-72 and 101-171, respectively.

Item 303. A computer-readable medium comprising computer instructions which, when executed by a processor, cause the processor to perform the method of item 302.

The invention claimed is:

1. An apparatus for extracorporeal blood treatment, comprising:
  an extracorporeal blood circuit and a connection system configured to connect the extracorporeal blood circuit to the vascular system of a patient, the extracorporeal blood circuit comprising:
  a blood processing device;
  at least first and second energy transfer sensors, the first energy transfer sensor associated with an arterial-side of the extracorporeal blood circuit, and the second energy transfer sensor associated with a venous-side of the extracorporeal blood circuit;
  at least one pumping device; and
  a control system configured to switch between a pre-treatment mode and a blood treatment mode, the control system configured in the blood treatment mode to operate said at least one pumping device to pump blood from the vascular system via the connection system through the blood processing device and back to the vascular system via the connection system, said control system comprising:
    an energy transfer sensor signal input device to obtain measurement data from said at least first and second energy transfer sensors configured to sense a transfer of energy comprising at least one pressure wave between the patient and the connection system or between the patient and the extracorporeal blood circuit, wherein the measurement data comprises first and second measurement signals from said first and second energy transfer sensors in the extracorporeal blood circuit; and
    a signal processor connected to the energy transfer sensor signal input device and being configured to, in the pre-treatment mode and post-priming prior to blood treatment, process the measurement data to detect connection of the extracorporeal blood circuit to the arterial-side and venous-side of the vascular system of the patient,
    wherein the connection is configured to be detected by said control system identifying a characteristic change in the measurement data indicating the connection of the extracorporeal blood circuit to the vascular system of the patient, and, upon such identification of the characteristic change, the control system is configured to take a dedicated action to control operation of the apparatus, the dedicated action comprising signaling the apparatus for entering into the blood treatment mode by operating said at least one pumping device only upon identification of the characteristic change in the first measurement signal and the second measurement signal.

2. The control system of claim 1, wherein the transfer of energy involves an electrical current.

3. The control system of claim 1, wherein the dedicated action further comprises automatically entering the blood treatment mode.

4. The control system of claim 1, wherein the dedicated action further comprises enabling manual start of the blood treatment mode.

5. The control system of claim 1, wherein the dedicated action comprises starting said at least one pumping device.

6. The control system of claim 1, wherein the connection system comprises an arterial access device for connecting the arterial-side of the extracorporeal blood circuit to the vascular system, and a venous access device for connecting the venous-side of the extracorporeal blood circuit to the vascular system.

7. The control system of claim 1, wherein the signal processor is configured to identify the characteristic change by identifying a step change in the measurement data.

8. The control system of claim 1, wherein the signal processor is configured to identify the characteristic change by identifying, in the measurement data, at least one pulse originating from a pulse generator.

9. The control system of claim 1, wherein said energy originates from an energy source associated with the patient, and wherein said at least one energy transfer sensor is associated with at least one of the extracorporeal blood circuit and the connection system.

10. The control system of claim 9, wherein the energy source comprises a physiological pulse generator in the patient.

11. The control system of claim 9, wherein said at least one energy transfer sensor is configured to detect a pressure wave generated by the energy source.

12. The control system of claim 11, wherein the measurement data comprises at least one first pulse representing the pressure wave and at least one interference pulse, wherein the signal processor is configured to process the measurement data to essentially eliminate said at least one interference pulse.

13. The control system of claim 1, wherein said energy originates from an energy source associated with the apparatus, and wherein said at least one energy transfer sensor is associated with the patient.

14. The control system of claim 13, wherein the energy source comprises the pumping device in the extracorporeal blood circuit.

15. A method for controlling an apparatus for extracorporeal blood treatment, comprising:

providing said apparatus comprising an extracorporeal blood circuit and a connection system configured to connect the extracorporeal blood circuit to the vascular system of a patient, the extracorporeal blood circuit comprising a blood processing device and at least one pumping device, said apparatus operable in a pre-treatment mode and a blood treatment mode;

obtaining measurement data from at least first and second energy transfer sensors which are configured to sense a transfer of energy comprising at least one pressure wave between the patient and the connection system or between the patient and the extracorporeal blood circuit, wherein the measurement data comprises first and second measurement signals from first and second energy transfer sensors in the extracorporeal blood circuit, wherein the first energy transfer sensor is associated with an arterial-side of the extracorporeal blood circuit, and the second energy transfer sensor is associated with a venous-side of the extracorporeal blood circuit, and wherein the signal processor is configured to take the dedicated action depending on the identification of the characteristic change in the first and second measurement signals;

operating the apparatus in the pre-treatment mode comprising priming the extracorporeal blood circuit and shutting off said at least one pumping device following completion of priming of the extracorporeal blood circuit;

processing the measurement data post-priming and prior to blood treatment while the at least one pumping device is shut off to detect connection of the extracorporeal blood circuit to the arterial-side and the venous-side of the vascular system of the patient; wherein the connection is detected by identifying a characteristic change in the measurement data indicating the connection of the extracorporeal blood circuit to the vascular system of the patient, wherein the connection is detected by identifying a characteristic change in the measurement data indicating the connection of the extracorporeal blood circuit to the vascular system of the patient; and upon such identification of the characteristic change in the measurement data post-priming and prior to blood treatment mode indicating connection of the extracorporeal blood circuit to the arterial-side and the venous-side of the vascular system of the patient, causing a dedicated action to control operation of the apparatus to be taken, wherein the dedicated action comprises allowing entry into the blood treatment mode; wherein the signal processor is configured to enable entry into the blood treatment mode only upon identification of the characteristic change in the first measurement signal and in the second measurement signal; and entering into the blood treatment mode including operating said at least one pumping device to pump blood from the vascular system via the connection system through the blood processing device and back to the vascular system via the connection system.

* * * * *